(12) United States Patent
Tan et al.

(10) Patent No.: US 10,660,652 B2
(45) Date of Patent: May 26, 2020

(54) ENDOSCOPIC SURGICAL CLIP APPLIER

(71) Applicant: Covidien LP, Mansfield, MA (US)

(72) Inventors: Yuandong Tan, Shanghai (CN); Kun Zhao, Shanghai (CN); Shunhong Xu, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 302 days.

(21) Appl. No.: 15/753,218

(22) PCT Filed: Oct. 10, 2015

(86) PCT No.: PCT/CN2015/091603
§ 371 (c)(1),
(2) Date: Feb. 16, 2018

(87) PCT Pub. No.: WO2017/059587
PCT Pub. Date: Apr. 13, 2017

(65) Prior Publication Data
US 2018/0242977 A1    Aug. 30, 2018

(51) Int. Cl.
*A61B 17/128* (2006.01)
*A61B 17/00* (2006.01)
*A61B 17/29* (2006.01)

(52) U.S. Cl.
CPC .. *A61B 17/1285* (2013.01); *A61B 2017/0046* (2013.01); *A61B 2017/00407* (2013.01);
(Continued)

(58) Field of Classification Search
CPC . A61B 17/1285; A61B 17/29; A61B 17/2909; A61B 2017/00367;
(Continued)

(56) References Cited

U.S. PATENT DOCUMENTS

| 4,226,242 A | 10/1980 | Jarvik |
| 4,418,694 A | 12/1983 | Beroff et al. |

(Continued)

FOREIGN PATENT DOCUMENTS

| AU | 2013254887 A1 | 11/2013 |
| CA | 1163889 A | 3/1984 |

(Continued)

OTHER PUBLICATIONS

Extended European Search Report dated May 29, 2019 corresponding to counterpart Patent Application EP 15905685.2.
(Continued)

*Primary Examiner* — Katherine M Rodjom

(57) ABSTRACT

A reposable endoscopic surgical clip applier includes a handle assembly (100) configured to releasably engage at least two different endoscopic assemblies (200,300,400). The handle assembly (100) is configured such that a ratcheting function thereof is disabled upon engagement of an endoscopic assembly (300) therewith that is not intended for ratcheting use and such that the ratcheting function is enabled upon engagement of an endoscopic assembly (400) therewith that is intended for ratcheting use. Endoscopic assemblies (200,300,400) for use with the handle assembly (100) are also provided.

17 Claims, 18 Drawing Sheets

(52) U.S. Cl.
CPC .......... *A61B 2017/00455* (2013.01); *A61B 2017/2902* (2013.01); *A61B 2017/2929* (2013.01)

(58) Field of Classification Search
CPC .. A61B 2017/00407; A61B 2017/0046; A61B 2017/00464; A61B 2017/2902
See application file for complete search history.

(56) References Cited

U.S. PATENT DOCUMENTS

| | | | |
|---|---|---|---|
| 4,471,780 A | 9/1984 | Menges et al. | |
| 4,726,372 A | 2/1988 | Perlin | |
| 4,834,096 A | 5/1989 | Oh et al. | |
| 5,030,226 A | 7/1991 | Green et al. | |
| 5,047,038 A | 9/1991 | Peters et al. | |
| 5,084,057 A | 1/1992 | Green et al. | |
| 5,100,420 A | 3/1992 | Green et al. | |
| 5,359,993 A | 11/1994 | Slater et al. | |
| 5,431,668 A | 7/1995 | Burbank, III et al. | |
| 5,448,042 A | 9/1995 | Robinson et al. | |
| 5,547,474 A | 8/1996 | Kloeckl et al. | |
| 5,562,655 A | 10/1996 | Mittelstadt et al. | |
| 5,607,436 A | 3/1997 | Pratt et al. | |
| 5,695,502 A | 12/1997 | Pier et al. | |
| 5,697,942 A | 12/1997 | Palti | |
| 5,743,310 A | 4/1998 | Moran | |
| 5,904,693 A | 5/1999 | Dicesare et al. | |
| 5,913,876 A | 6/1999 | Taylor et al. | |
| 5,921,991 A | 7/1999 | Whitehead et al. | |
| 5,951,574 A | 9/1999 | Stefanchik et al. | |
| 6,044,971 A | 4/2000 | Esposito et al. | |
| 6,053,908 A | 4/2000 | Crainich et al. | |
| 6,228,097 B1 | 5/2001 | Levinson et al. | |
| 6,306,149 B1 | 10/2001 | Meade | |
| 6,824,547 B2 | 11/2004 | Wilson, Jr. et al. | |
| 7,297,149 B2 | 11/2007 | Vitali et al. | |
| 7,585,304 B2 | 9/2009 | Hughett | |
| 7,740,641 B2 | 6/2010 | Huitema | |
| 7,819,886 B2 | 10/2010 | Whitfield et al. | |
| 7,905,890 B2 | 3/2011 | Whitfield et al. | |
| 8,048,088 B2 | 11/2011 | Green et al. | |
| 8,075,571 B2 | 12/2011 | Vitali et al. | |
| 8,216,257 B2 | 7/2012 | Huitema et al. | |
| 8,236,012 B2 | 8/2012 | Molitor et al. | |
| 8,246,634 B2 | 8/2012 | Huitema et al. | |
| 8,246,635 B2 | 8/2012 | Huitema | |
| 8,328,822 B2 | 12/2012 | Huitema et al. | |
| 8,403,138 B2 | 3/2013 | Weisshaupt et al. | |
| 8,403,945 B2 | 3/2013 | Whitfield et al. | |
| 8,403,946 B2 | 3/2013 | Whitfield et al. | |
| 8,419,752 B2 | 4/2013 | Sorrentino et al. | |
| 8,430,892 B2 | 4/2013 | Bindra et al. | |
| 8,486,091 B2 | 7/2013 | Sorrentino et al. | |
| 8,491,608 B2 | 7/2013 | Sorrentino et al. | |
| 8,496,673 B2 | 7/2013 | Nguyen et al. | |
| 8,545,486 B2 | 10/2013 | Malkowski | |
| 8,585,717 B2 | 11/2013 | Sorrentino et al. | |
| 8,734,469 B2 | 5/2014 | Pribanic et al. | |
| 8,753,356 B2 | 6/2014 | Vitali et al. | |
| 8,821,516 B2 | 9/2014 | Huitema | |
| 8,845,659 B2 | 9/2014 | Whitfield et al. | |
| 8,894,665 B2 | 11/2014 | Sorrentino et al. | |
| 8,915,930 B2 | 12/2014 | Huitema et al. | |
| 8,939,974 B2 | 1/2015 | Boudreaux et al. | |
| 9,011,464 B2 | 4/2015 | Zammataro | |
| 9,089,334 B2 | 7/2015 | Sorrentino et al. | |
| 9,186,136 B2 | 11/2015 | Malkowski et al. | |
| 9,186,153 B2 | 11/2015 | Zammataro | |
| 9,220,507 B1 | 12/2015 | Patel et al. | |
| 9,282,972 B1 | 3/2016 | Patel et al. | |
| 9,358,011 B2 | 6/2016 | Sorrentino et al. | |
| 9,393,024 B2 | 7/2016 | Whitfield et al. | |
| 9,408,610 B2 | 8/2016 | Hartoumbekis | |
| 9,414,844 B2 | 8/2016 | Zergiebel et al. | |
| 9,445,810 B2 | 9/2016 | Cappola | |
| 9,498,227 B2 | 11/2016 | Zergiebel et al. | |
| 9,526,501 B2 | 12/2016 | Malkowski | |
| 9,526,565 B2 | 12/2016 | Strobl | |
| 9,545,254 B2 | 1/2017 | Sorrentino et al. | |
| 9,561,038 B2 | 2/2017 | Shelton, IV et al. | |
| 9,642,627 B2 | 5/2017 | Zammataro | |
| 9,687,247 B2 | 6/2017 | Aranyi et al. | |
| 9,717,504 B2 | 8/2017 | Huitema | |
| 9,717,505 B2 | 8/2017 | Whitfield et al. | |
| 9,737,310 B2 | 8/2017 | Whitfield et al. | |
| 9,750,500 B2 | 9/2017 | Malkowski | |
| 9,763,668 B2 | 9/2017 | Whitfield et al. | |
| 9,775,623 B2 | 10/2017 | Zammataro et al. | |
| 9,775,624 B2 | 10/2017 | Rockrohr et al. | |
| 9,782,181 B2 | 10/2017 | Vitali et al. | |
| 9,848,886 B2 | 12/2017 | Malkowski et al. | |
| 9,855,043 B2 | 1/2018 | Malkowski | |
| 9,931,124 B2 | 4/2018 | Gokharu | |
| 9,968,361 B2 | 5/2018 | Aranyi et al. | |
| 9,968,362 B2 | 5/2018 | Malkowski et al. | |
| 10,004,502 B2 | 6/2018 | Malkowski et al. | |
| 10,136,939 B2 | 11/2018 | Minnelli et al. | |
| 10,159,484 B2 | 12/2018 | Sorrentino et al. | |
| 10,159,491 B2 | 12/2018 | Gokharu | |
| 10,159,492 B2 | 12/2018 | Zammataro | |
| 10,166,027 B2 | 1/2019 | Aranyi et al. | |
| 10,231,732 B1 | 3/2019 | Racenet et al. | |
| 10,231,735 B2 | 3/2019 | Sorrentino et al. | |
| 10,231,738 B2 | 3/2019 | Sorrentino et al. | |
| 10,258,346 B2 | 4/2019 | Zergiebel et al. | |
| 10,292,712 B2 | 5/2019 | Shankarsetty | |
| 10,349,936 B2 | 7/2019 | Rockrohr et al. | |
| 10,349,950 B2 | 7/2019 | Aranyi et al. | |
| 10,357,250 B2 | 7/2019 | Zammataro | |
| 10,363,045 B2 | 7/2019 | Whitfield et al. | |
| 10,368,876 B2 | 8/2019 | Bhatnagar et al. | |
| 10,390,831 B2 | 8/2019 | Holsten et al. | |
| 10,426,489 B2 | 10/2019 | Baril | |
| 2002/0123742 A1 | 9/2002 | Baxter et al. | |
| 2003/0014060 A1 | 1/2003 | Wilson et al. | |
| 2004/0097970 A1 | 5/2004 | Hughett | |
| 2004/0097971 A1 | 5/2004 | Hughett | |
| 2004/0232197 A1 | 11/2004 | Shelton et al. | |
| 2005/0006432 A1 | 1/2005 | Racenet et al. | |
| 2005/0171560 A1 | 8/2005 | Hughett | |
| 2006/0000867 A1 | 1/2006 | Shelton et al. | |
| 2006/0079115 A1 | 4/2006 | Aranyi | |
| 2006/0085021 A1 | 4/2006 | Wenzler | |
| 2006/0124485 A1 | 6/2006 | Kennedy | |
| 2006/0235439 A1 | 10/2006 | Molitor et al. | |
| 2006/0241655 A1 | 10/2006 | Viola | |
| 2007/0021766 A1 | 1/2007 | Belagali et al. | |
| 2007/0093790 A1 | 4/2007 | Downey et al. | |
| 2008/0004636 A1 | 1/2008 | Walberg et al. | |
| 2008/0083813 A1 | 4/2008 | Zemlok et al. | |
| 2009/0204115 A1 | 8/2009 | Dees, Jr. et al. | |
| 2009/0209946 A1 | 8/2009 | Swayze et al. | |
| 2009/0261142 A1 | 10/2009 | Milliman et al. | |
| 2009/0264904 A1 | 10/2009 | Aldrich et al. | |
| 2009/0312775 A1 | 12/2009 | Gilkey et al. | |
| 2010/0057103 A1 | 3/2010 | Sorrentino et al. | |
| 2010/0057106 A1* | 3/2010 | Sorrentino | A61B 17/10 606/143 |
| 2010/0089970 A1 | 4/2010 | Smith et al. | |
| 2010/0318103 A1 | 12/2010 | Cheng et al. | |
| 2010/0331862 A1 | 12/2010 | Monassevitch et al. | |
| 2011/0087220 A1 | 4/2011 | Felder et al. | |
| 2011/0087268 A1 | 4/2011 | Livneh | |
| 2011/0208211 A1 | 8/2011 | Whitfield et al. | |
| 2012/0022526 A1 | 1/2012 | Aldridge et al. | |
| 2012/0226291 A1 | 9/2012 | Malizia et al. | |
| 2012/0253298 A1 | 10/2012 | Henderson et al. | |
| 2013/0041379 A1 | 2/2013 | Bodor et al. | |
| 2013/0172909 A1 | 7/2013 | Harris | |
| 2013/0172910 A1 | 7/2013 | Malkowski | |
| 2013/0175320 A1 | 7/2013 | Mandakolathur Vasudevan et al. | |
| 2013/0226200 A1 | 8/2013 | Kappel et al. | |
| 2013/0253540 A1 | 9/2013 | Castro et al. | |

(56) References Cited

U.S. PATENT DOCUMENTS

| | | |
|---|---|---|
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0194903 A1 | 7/2014 | Malkowski et al. |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0190138 A1 | 7/2015 | Whitfield et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 1994236 A | 7/2007 |
| CN | 101530340 A | 9/2009 |
| CN | 103083059 A | 5/2013 |
| CN | 103251441 A | 8/2013 |
| CN | 104487006 A | 4/2015 |
| CN | 104605911 B | 2/2017 |
| DE | 202007003398 U1 | 6/2007 |
| EP | 3132756 A1 | 2/2017 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2009.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.

(56) References Cited

OTHER PUBLICATIONS

Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
International Search Report for PCT/CN2015/091603 date of completion is Jun. 20, 2016 (3 pages).
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Japanese Office Action dated Aug. 21, 2019 corresponding to counterpart Patent Application JP 2018-516433.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

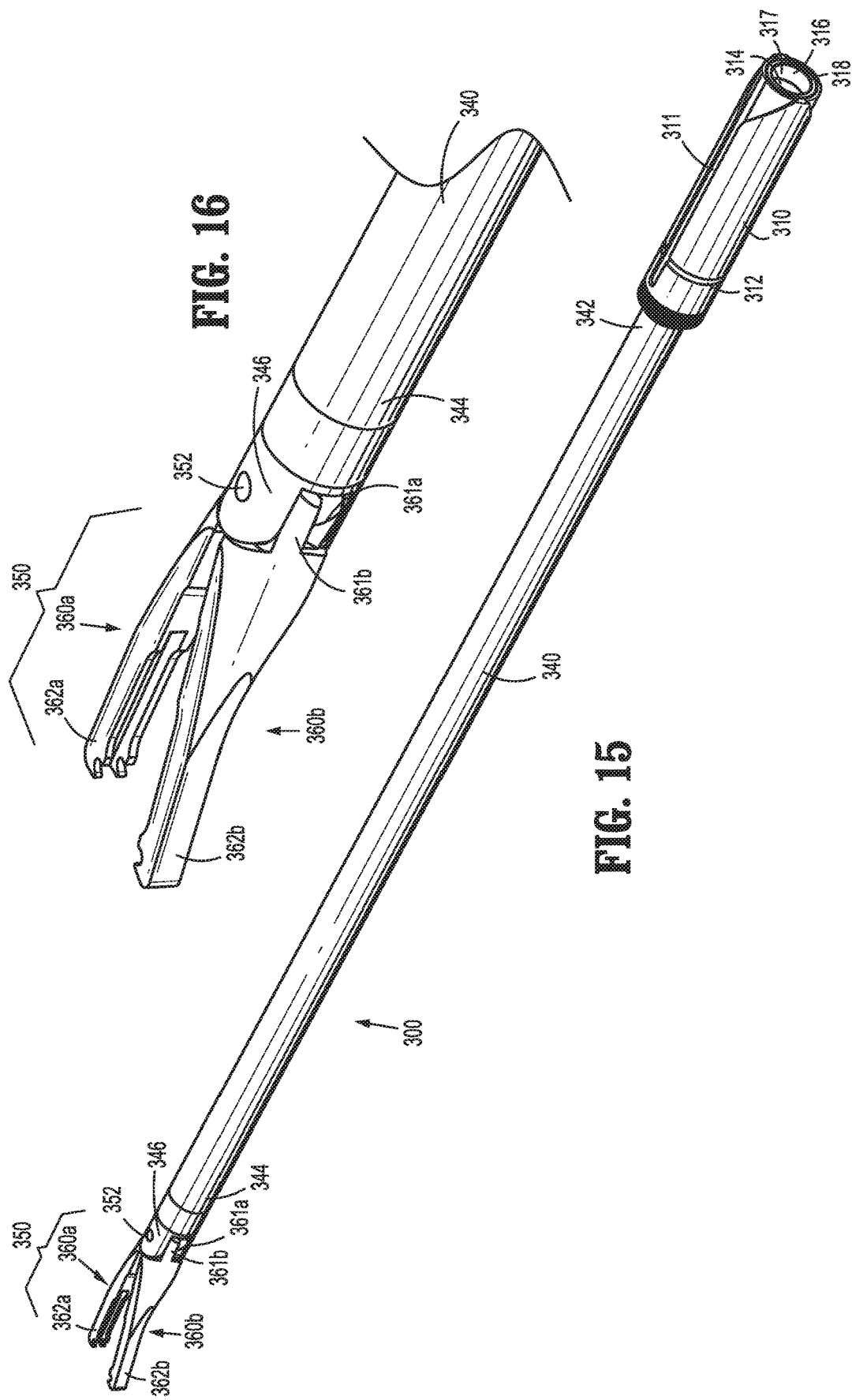

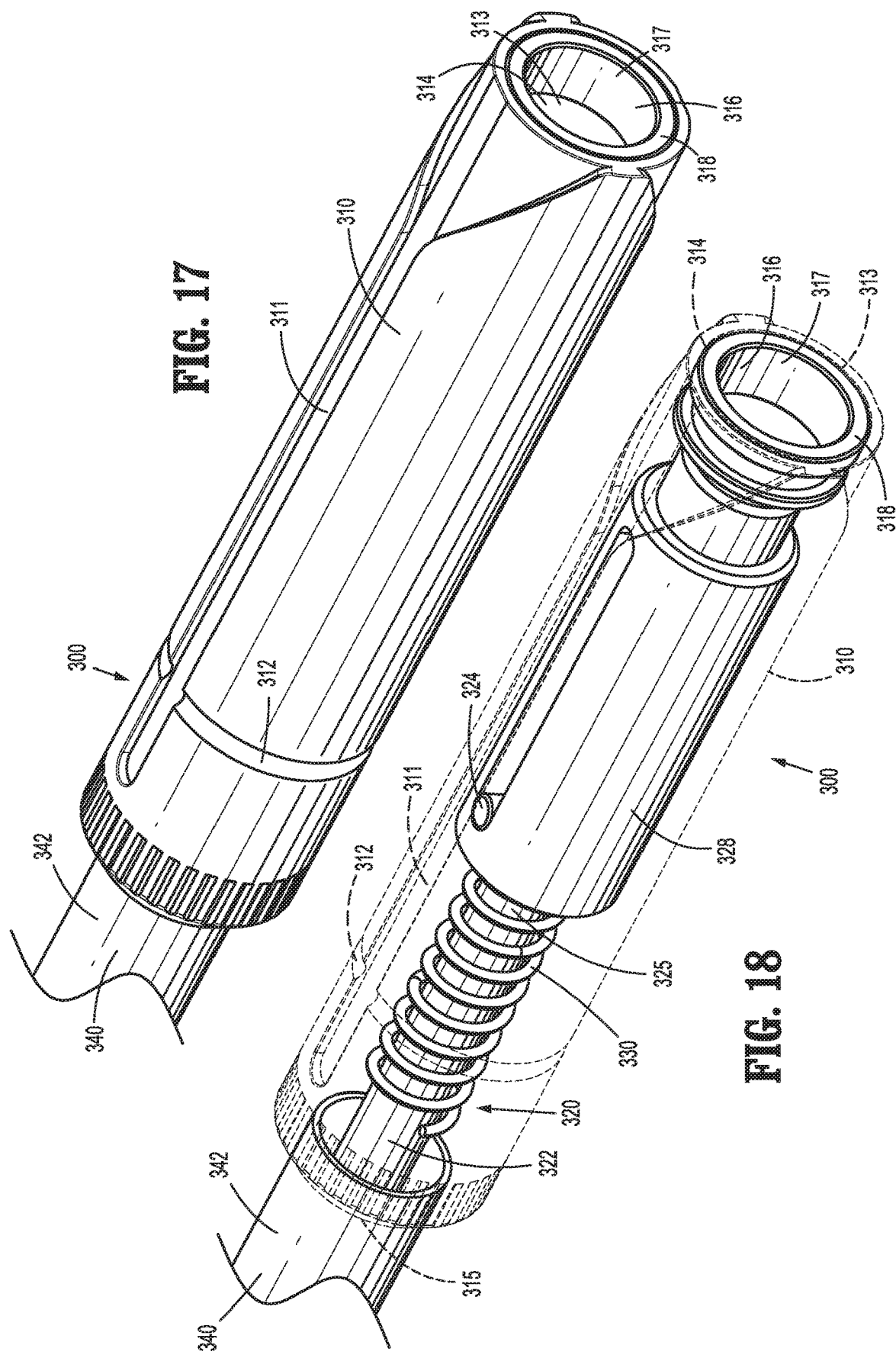

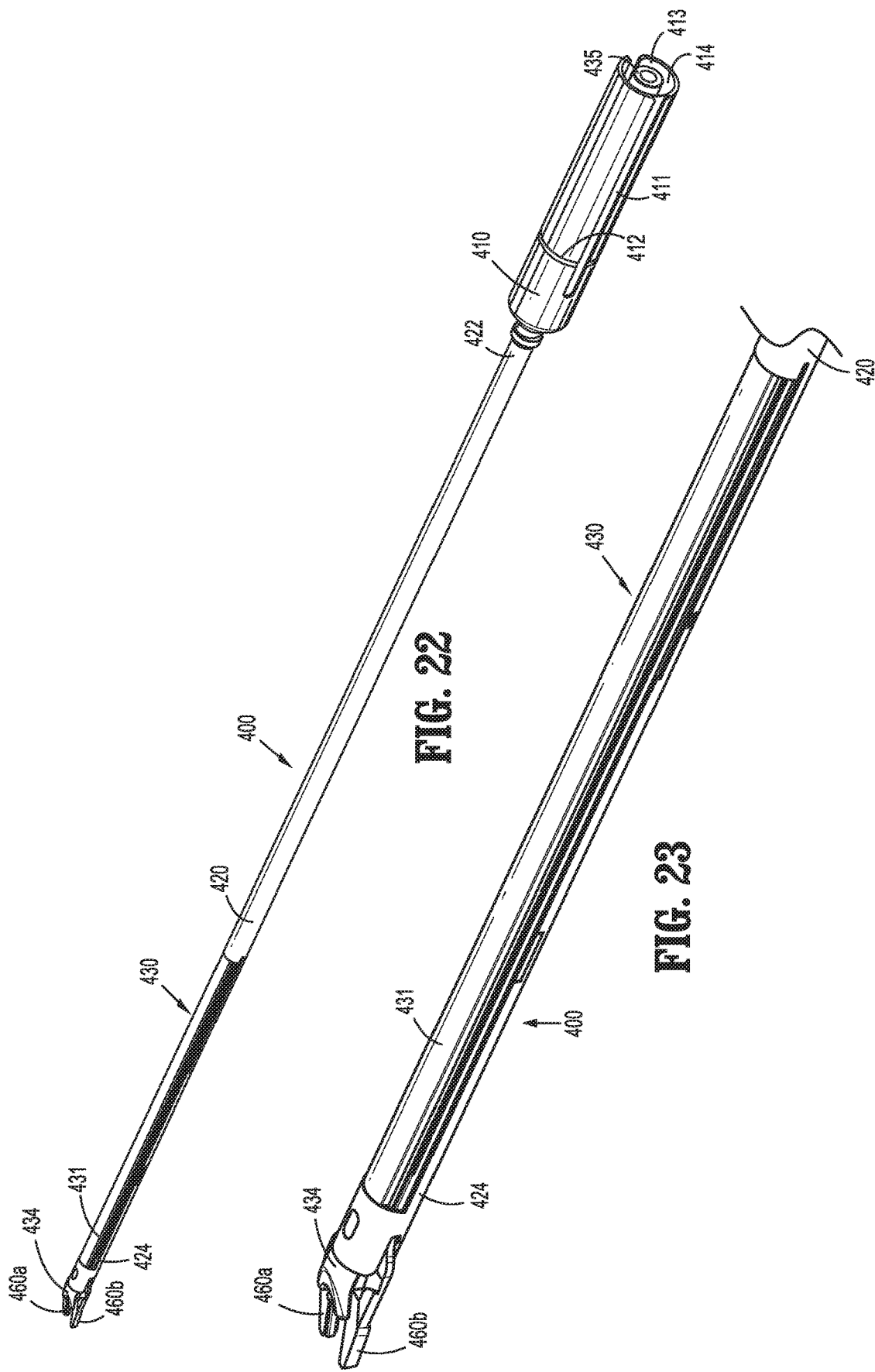

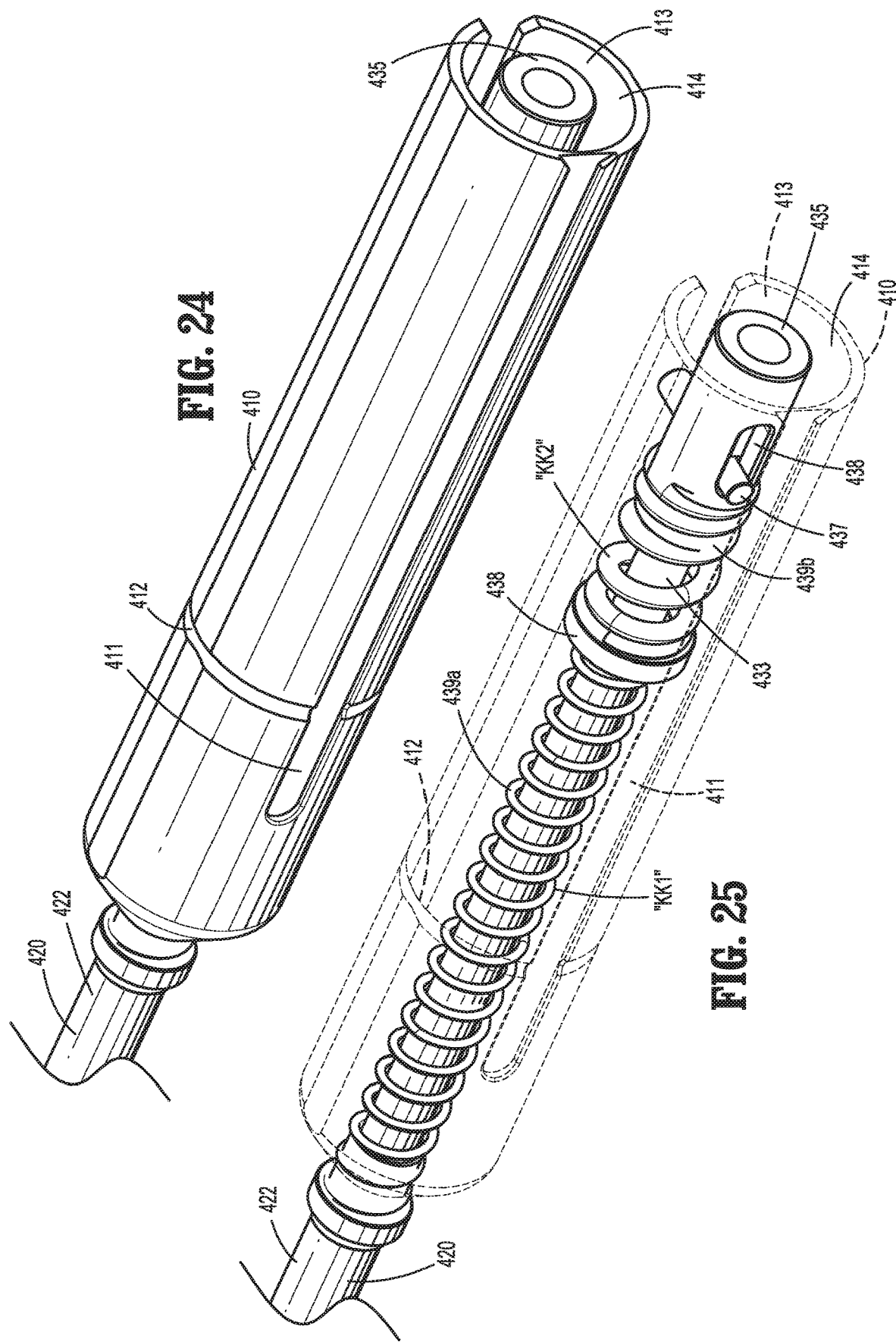

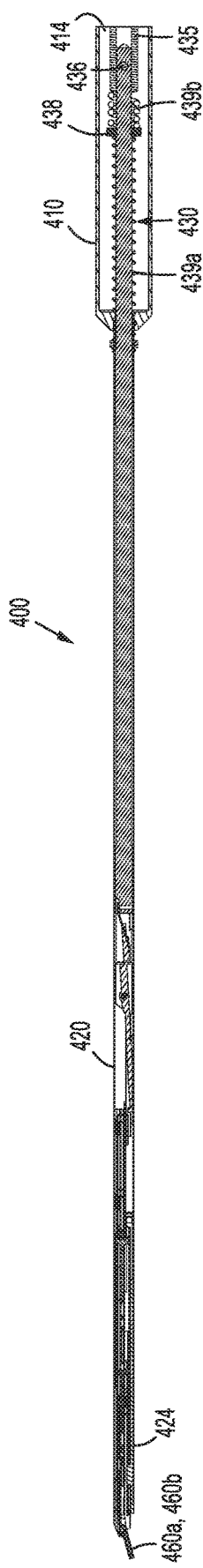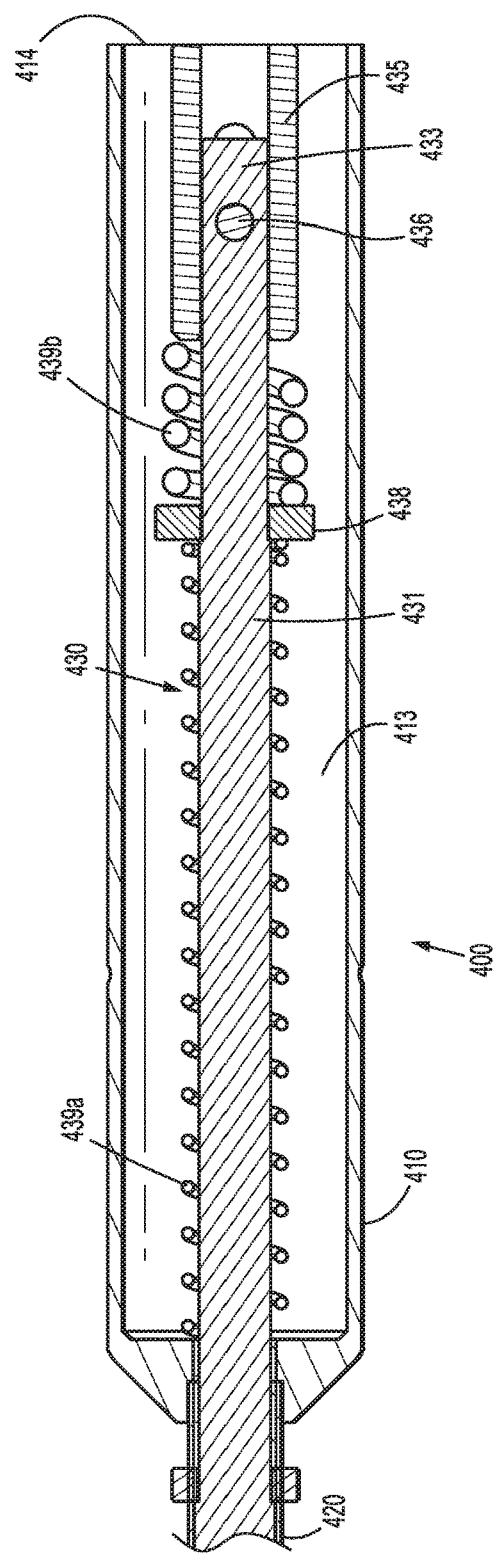
FIG. 26
FIG. 27

ENDOSCOPIC SURGICAL CLIP APPLIER

CROSS-REFERENCE TO RELATED APPLICATION

This application is a National Stage Application of PCT/CN2015/091603 under 35USC § 371 (a), the disclosure of the above-identified application is hereby incorporated by reference in its entirety.

BACKGROUND

Technical Field

The technical field relates to surgical clip appliers. More particularly, the present disclosure relates to endoscopic surgical clip appliers having handle assemblies configured for use with various different endoscopic assemblies.

Description of Related Art

Endoscopic surgical staplers and surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often use a particular endoscopic surgical clip applier to apply a surgical clip to a blood vessel or another duct to prevent the flow of body fluids therethrough during the procedure.

Endoscopic surgical clip appliers having various sizes (e.g., diameters), that are configured to apply a variety of diverse surgical clips, are known in the art, and which are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

Endoscopic surgical clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic surgical clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable endoscopic surgical clip applier. The endoscopic surgical clip applier advances and forms multiple clips during a single insertion into the body cavity. This resterilizable endoscopic surgical clip applier is configured to receive and cooperate with an interchangeable clip magazine so as to advance and form multiple clips during a single entry into a body cavity.

During endoscopic or laparoscopic procedures it may be desirable and/or necessary to use different size surgical clips or different configured surgical clips depending on the underlying tissue or vessels to be ligated. In order to reduce overall costs of an endoscopic surgical clip applier, it is desirable for a single endoscopic surgical clip applier to be loadable with and capable of firing different size surgical clips as needed.

Accordingly, a need exists for endoscopic surgical clip appliers that include handle assemblies configured for use with various different endoscopic assemblies having different clips loaded therein and/or configured for performing various different surgical tasks.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is a handle assembly of a reposable surgical clip applier configured to releasably engage at least two different endoscopic assemblies. The handle assembly includes a housing, a trigger, a drive bar, a ratchet pawl, a receiver assembly, and a bypass assembly. The housing defines a body portion and a fixed handle portion extending from the body portion. The trigger is pivotably connected to the housing and movable relative to the fixed handle portion between an un-actuated position and an actuated position. The drive bar is slidably supported within the body portion of the housing and operably coupled to the trigger such that movement of the trigger from the un-actuated position towards the actuated position translates the drive bar distally through the body portion of the housing. The drive bar further includes a ratchet rack disposed thereon. The ratchet pawl is pivotably supported within the housing and movable relative thereto between a use position, wherein the ratchet pawl is positioned to engage the ratchet rack upon distal translation of the drive bar, and a bypass position, wherein the ratchet pawl is displaced from the ratchet rack to inhibit engagement therewith upon distal translation of the drive bar. The receiver assembly is configured to releasably engage an endoscopic assembly therein. The bypass assembly is operably positioned between the receiver assembly and the ratchet pawl and configured such that, upon insertion of a first type of endoscopic assembly into engagement with the receiver assembly, the bypass assembly urges the ratchet pawl to move to the bypass position to disable ratcheting during distal translation of the drive bar, and such that, upon insertion of a second type of endoscopic assembly into engagement with the receiver assembly, the bypass assembly is undisturbed such that the ratchet pawl remains disposed in the use position to enabling ratcheting during distal translation of the drive bar.

In aspects of the present disclosure, the bypass assembly includes a sleeve defining a distal rim configured to interfere with the first type of endoscopic assembly upon insertion of the first type of endoscopic assembly into the receiver assembly such that the first type of endoscopic assembly urges the sleeve proximally to thereby move the ratchet pawl from the use position to the bypass position.

In aspects of the present disclosure, the sleeve of the bypass assembly is configured for insertion into an opening defined within the second type of endoscopic assembly upon insertion of the second type of endoscopic assembly into the receiver assembly such that the sleeve is maintained in position.

In aspects of the present disclosure, the bypass assembly further includes a biasing member configured to bias the sleeve distally such that the sleeve is maintained in position in the absence of proximal urging applied thereto.

In aspects of the present disclosure, a pawl biasing member is provided for biasing the ratchet pawl towards the use position.

In aspects of the present disclosure, the receiver assembly including an inner tubular member configured to releasably receive a proximal portion of the first type of endoscopic assembly and a proximal portion of the second type of endoscopic assembly. The inner tubular member includes at least one alignment member configured to align the proximal portion of the endoscopic assembly inserted therein, and at least one engagement member configured to releasably engage the proximal portion of the endoscopic assembly inserted therein.

In aspects of the present disclosure, the drive bar defines a proximal recess disposed proximally of the ratchet rack and a distal recess disposed distally of the ratchet rack. In such aspects, in the un-actuated position of the trigger and the use position of the ratchet pawl, the drive bar is positioned such that the ratchet pawl is at least partially disposed within the distal recess. Further, in an intermediate position of the trigger between the un-actuated and actuated positions thereof, and the use position of the ratchet pawl, the drive bar is positioned such that ratchet pawl is engaged with the ratchet rack to inhibit return of the trigger towards the un-actuated position. Further still, in the actuated position of the trigger and the use position of the ratchet pawl, the drive bar is positioned such that the ratchet pawl is at least partially disposed within the proximal recess to permit the trigger to be returned to the un-actuated position.

A reposable surgical clip applier or system provided in accordance with aspects of the present disclosure includes a handle assembly and a first endoscopic assembly and/or a second endoscopic assembly. The handle assembly includes a housing, a trigger, a drive bar, a ratchet pawl, a receiver assembly, and a bypass assembly, any or all of which may be configured similarly as detailed above. The bypass assembly is movable between a distal position and a proximal position for moving the ratchet pawl between the use position and the bypass position. The handle assembly is configured to receive and engage a first endoscopic assembly and/or an second endoscopic assembly therein.

In aspects, the first endoscopic assembly is configured for ratcheting use and includes a proximal hub insertable into and releasably engagable within the receiver assembly of the handle assembly, an elongated shaft extending distally from the proximal hub, an end effector assembly supported at a distal end of the elongated shaft, and an inner drive assembly disposed within the proximal hub and the elongated shaft and operably coupled to the end effector assembly such that actuation of the inner drive assembly manipulates the end effector assembly. The proximal hub and the inner drive assembly of the first endoscopic assembly define an annular gap therebetween. The annular gap is configured to receive a portion of the bypass assembly upon insertion of the first endoscopic assembly into the receiver assembly such that the bypass assembly is maintained in the distal position upon engagement of the proximal hub within the receiver assembly, thereby maintaining the ratchet pawl in the use position and enabling engagement of the ratchet pawl with the ratchet rack during distal translation of the drive bar.

In aspects, the second endoscopic assembly is configured for non-ratcheting use and includes a proximal hub insertable into and releasably engagable within the receiver assembly of the handle assembly and defining a proximally-facing surface. The second endoscopic assembly further includes an elongated shaft extending distally from the proximal hub, an end effector assembly supported at a distal end of the elongated shaft, and an inner drive assembly disposed within the proximal hub and the elongated shaft and operably coupled to the end effector assembly such that actuation of the inner drive assembly manipulates the end effector assembly. The proximally-facing surface of the proximal hub is positioned such that, upon insertion of the second endoscopic assembly into the receiver assembly, the proximally-facing surface is urged into contact with the bypass assembly to move the bypass assembly from the distal position to the proximal position to thereby pivot the ratchet pawl from the use position to the bypass position to inhibit engagement of the ratchet pawl with the ratchet rack during distal translation of the drive bar.

In aspects of the present disclosure, upon movement of the trigger from the un-actuated position to an intermediate position between the un-actuated position and the actuated position with the first endoscopic assembly engaged with the handle assembly, the drive bar is positioned such that ratchet pawl is engaged with the ratchet rack to inhibit return of the trigger towards the un-actuated position.

In aspects of the present disclosure, with the second endoscopic assembly engaged with the handle assembly, the trigger is permitted to return towards the actuated position at each point between the un-actuated position and the actuated position.

BRIEF DESCRIPTION OF THE DRAWINGS

Aspects and features of the presently-disclosed endoscopic surgical clip applier are described in detail with reference to the drawing figures wherein like reference numerals identify similar or identical structural elements and:

FIG. 15 is a perspective view of another endoscopic assembly configured for use with the handle assembly of FIG. 1;

FIG. 16 is an enlarged, perspective view of the distal portion of the endoscopic assembly of FIG. 15;

FIG. 17 is an enlarged, perspective view of the proximal portion of the endoscopic assembly of FIG. 15;

FIG. 18 is an enlarged, perspective, of the proximal portion of the endoscopic assembly of FIG. 15 with a portion of the outer housing shown in phantom to illustrate the internal components therein;

FIG. 22 is a perspective view of another endoscopic assembly configured for use with the handle assembly of FIG. 1;

FIG. 23 is an enlarged, perspective view of the distal portion of the endoscopic assembly of FIG. 22;

FIG. 24 is an enlarged, perspective view of the proximal portion of the endoscopic assembly of FIG. 22;

FIG. 25 is an enlarged, perspective, of the proximal portion of the endoscopic assembly of FIG. 22 with a portion of the outer housing shown in phantom to illustrate the internal components therein;

FIG. 26 is a longitudinal, cross-sectional view of the endoscopic assembly of FIG. 22;

FIG. 27 is a longitudinal, cross-sectional view of the proximal portion of the endoscopic assembly of FIG. 22;

DETAILED DESCRIPTION OF EMBODIMENTS

Figure 1:
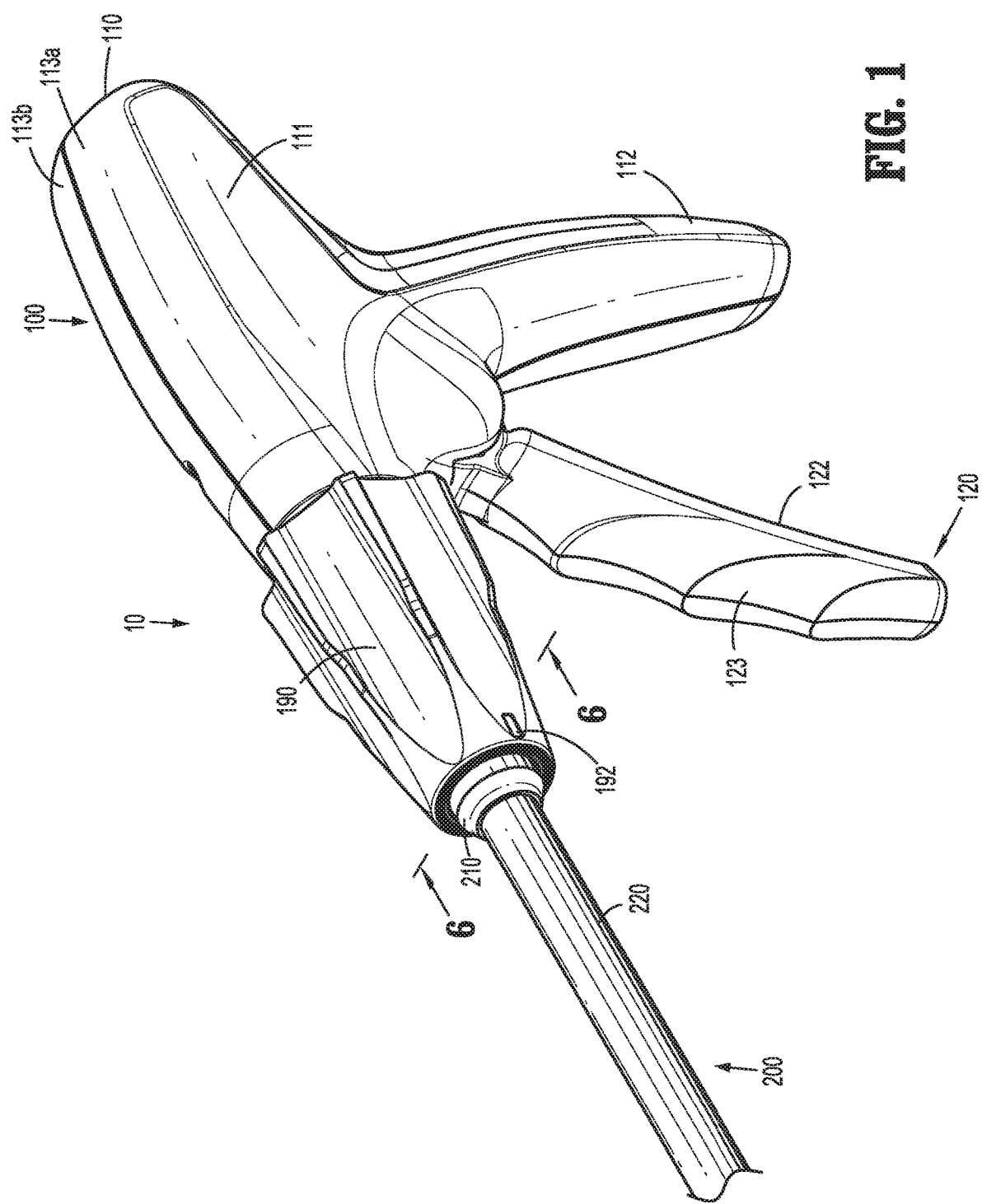
FIG. 1 is a perspective view of the proximal portion of an endoscopic surgical clip applier provided in accordance with the present disclosure including a handle assembly having an endoscopic assembly engaged therewith.
Figure 2:
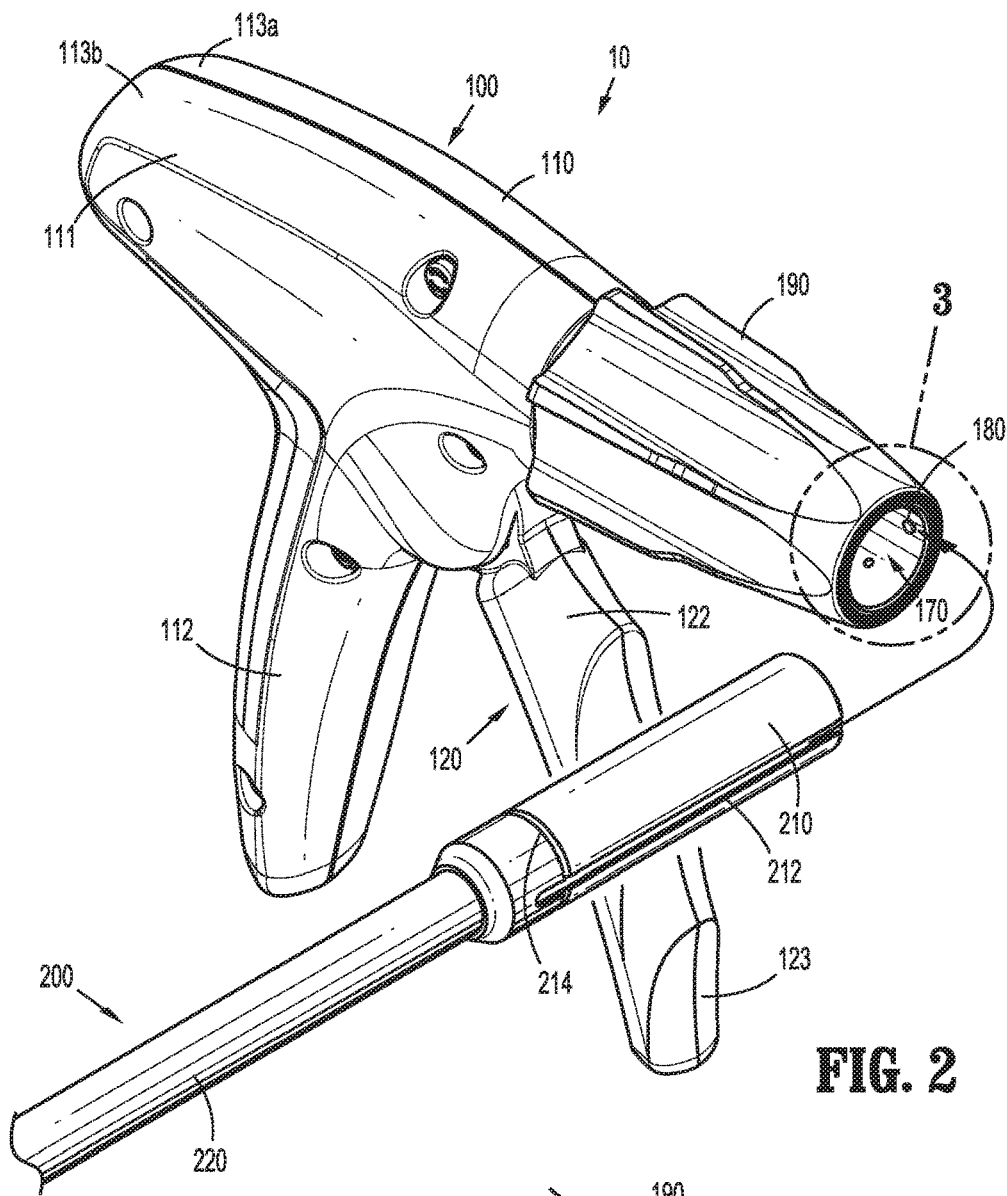
FIG. 2 is perspective view of the endoscopic surgical clip applier of FIG. 1 with the endoscopic assembly removed from the handle assembly.

Turning to FIGS. 1 and 2, an endoscopic surgical clip applier provided in accordance with the present disclosure is identified by reference numeral 10. Surgical clip applier 10 generally includes a handle assembly 100 and a plurality of endoscopic assemblies 200 selectively connectable to and extendable distally from handle assembly 100. Handle assembly 100 is advantageously configured to operate each of the plurality of endoscopic assemblies 200, upon connection thereto, and may be configured as a sterilizable, reusable component such that handle assembly 100 may be repeatedly used with different and/or additional endoscopic assemblies 200 during the course of one or more surgical procedures. The endoscopic assemblies 200 may be configured as single-use disposable components, limited-use disposable components, or reusable components, depending upon a particular purpose and/or the configuration of the particular endoscopic assembly 200. In either configuration, the need for multiple handle assemblies 100 is obviated and, instead, the surgeon need only select an appropriate endoscopic assembly 200 and connect that endoscopic assembly 200 to handle assembly 100 in preparation for use.

Handle assembly 100 is initially detailed for use in connection with a generic endoscopic assembly 200 that includes features common to any endoscopic assembly usable with handle assembly 100. Exemplary embodiments of particular endoscopic assemblies, e.g., endoscopic assembly 300 (FIG. 15) and endoscopic assembly 400 (FIG. 22), are thereafter detailed below. Endoscopic assembly 300 (FIG. 15), for example, is configured for grasping and manipulating tissue, retrieving a surgical clip, and firing and forming the surgical clip about tissue. Endoscopic assembly 400 (FIG. 22), as another example, includes at least one surgical clip loaded therein and is configured to sequentially fire and form the at least one surgical clip about tissue. It is also envisioned that various other endoscopic assemblies for performing various different surgical tasks and/or having various different configurations may be provided for use with handle assembly 100.

Continuing with reference to FIGS. 1 and 2, as noted above, endoscopic assembly 200 is configured to selectively connect to and extend distally from handle assembly 100. Endoscopic assembly 200 includes a proximal hub 210 configured for insertion into and releasable engagement within handle assembly 100, an elongated shaft 220 extending distally from proximal hub 210, and an end effector assembly (not shown) disposed at the distal end of elongated shaft 220. Internal drive components (not shown) extend through proximal hub 210 and elongated shaft 220 so as to operably couple the end effector assembly (not shown) with handle assembly 100 upon engagement of endoscopic assembly 200 with handle assembly 100, e.g., to enable performing the one or more surgical tasks of the endoscopic assembly 200. Proximal hub 210 defines a generally tubular configuration and includes a longitudinally-extending slot 212 defined therein and an annular groove 214 defined therein. Longitudinally-extending slot 212 defines an open proximal end 213. Annular groove 214 extends circumferentially about proximal hub 210 and intersects longitudinally-extending slot 212, although other non-intersecting configurations are also contemplated.

Figure 3:
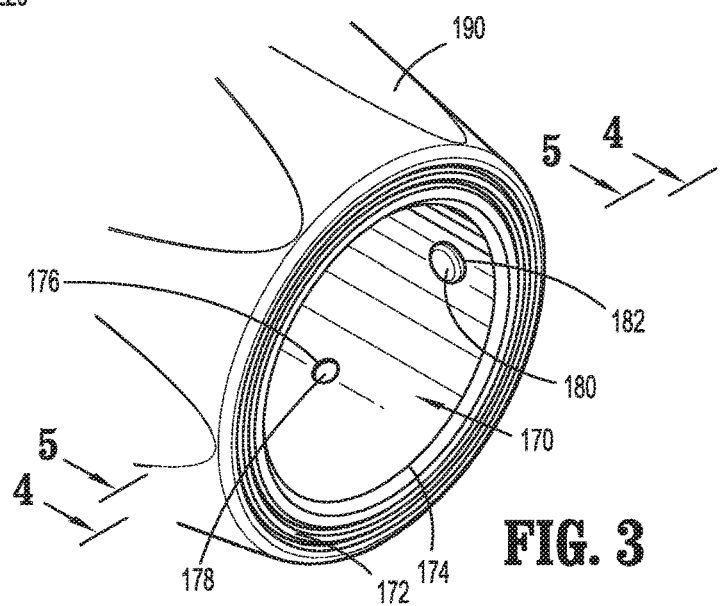
FIG. 3 is an enlarged, perspective view of the area of detail indicated as "3" in FIG. 2.
Figure 4:
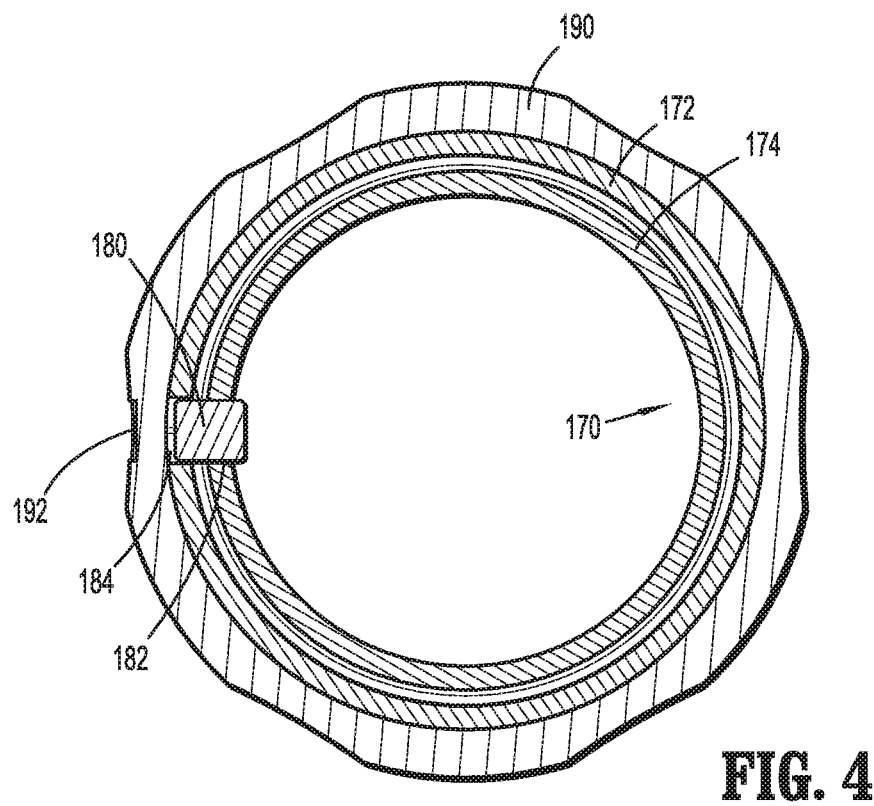
FIG. 4 is a transverse, cross-sectional view taken across section line 4-4 in FIG. 3.
Figure 5:
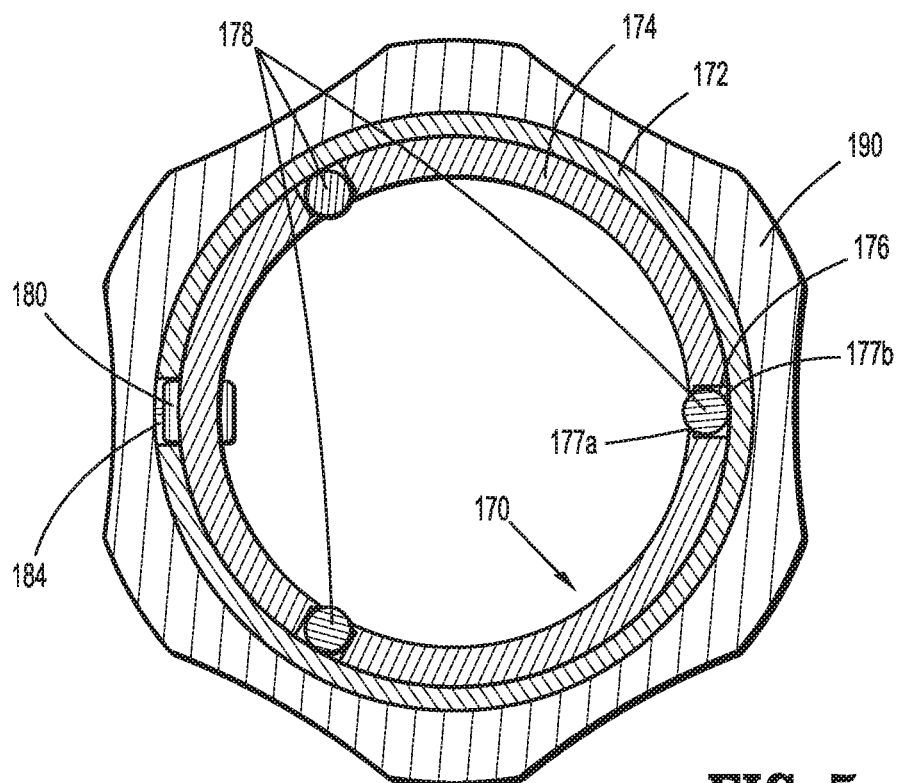
FIG. 5 is a transverse, cross-sectional view taken across section line 5-5 in FIG. 3.
Figure 6:
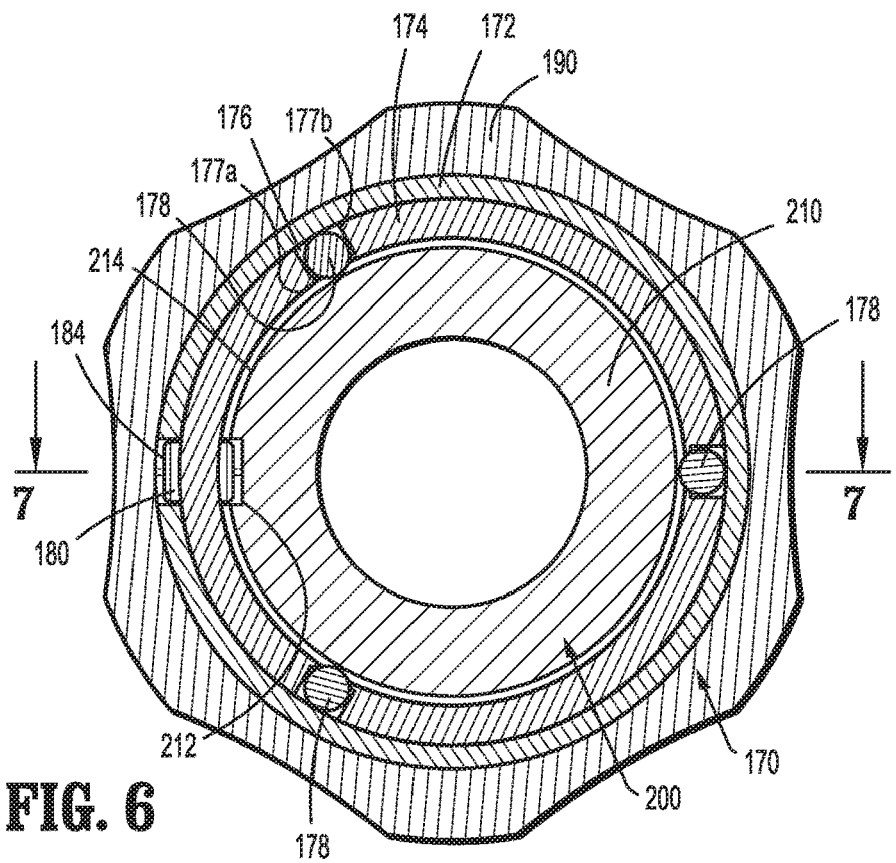
FIG. 6 is a transverse, cross-sectional view taken across section line 6-6 in FIG. 1.
Figure 7:
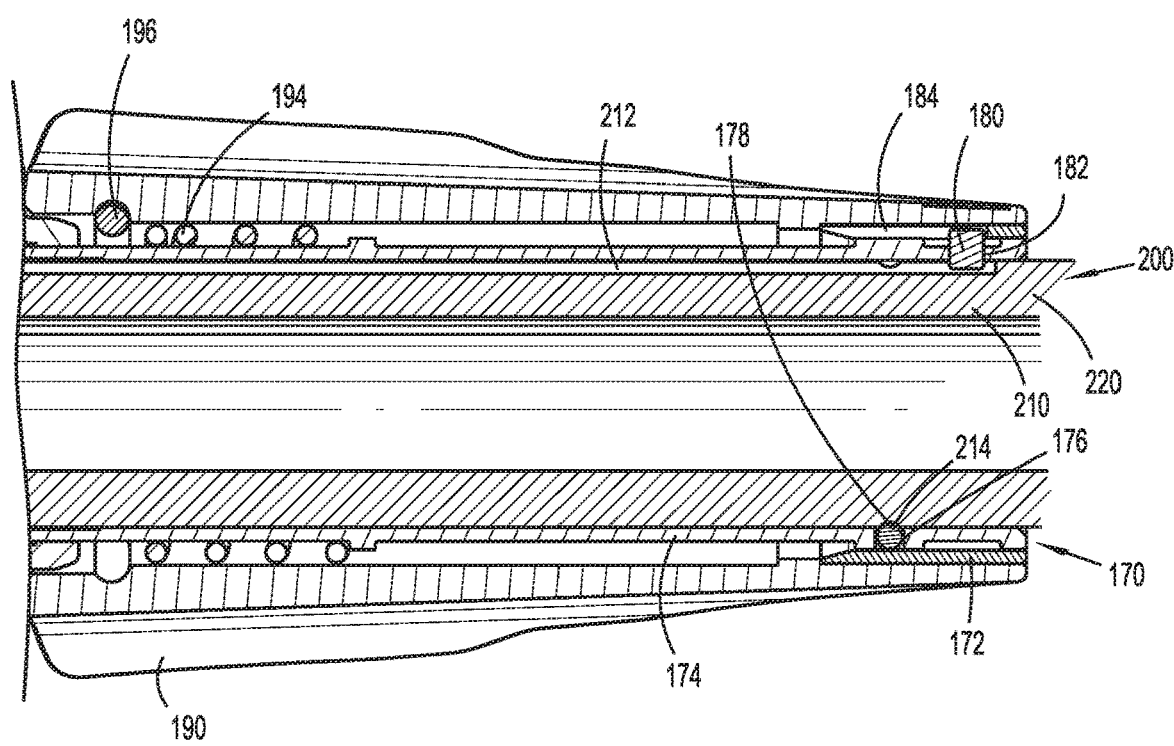
FIG. 7 is a longitudinal, cross-sectional view taken across section line 7-7 in FIG. 6.
Figure 8:
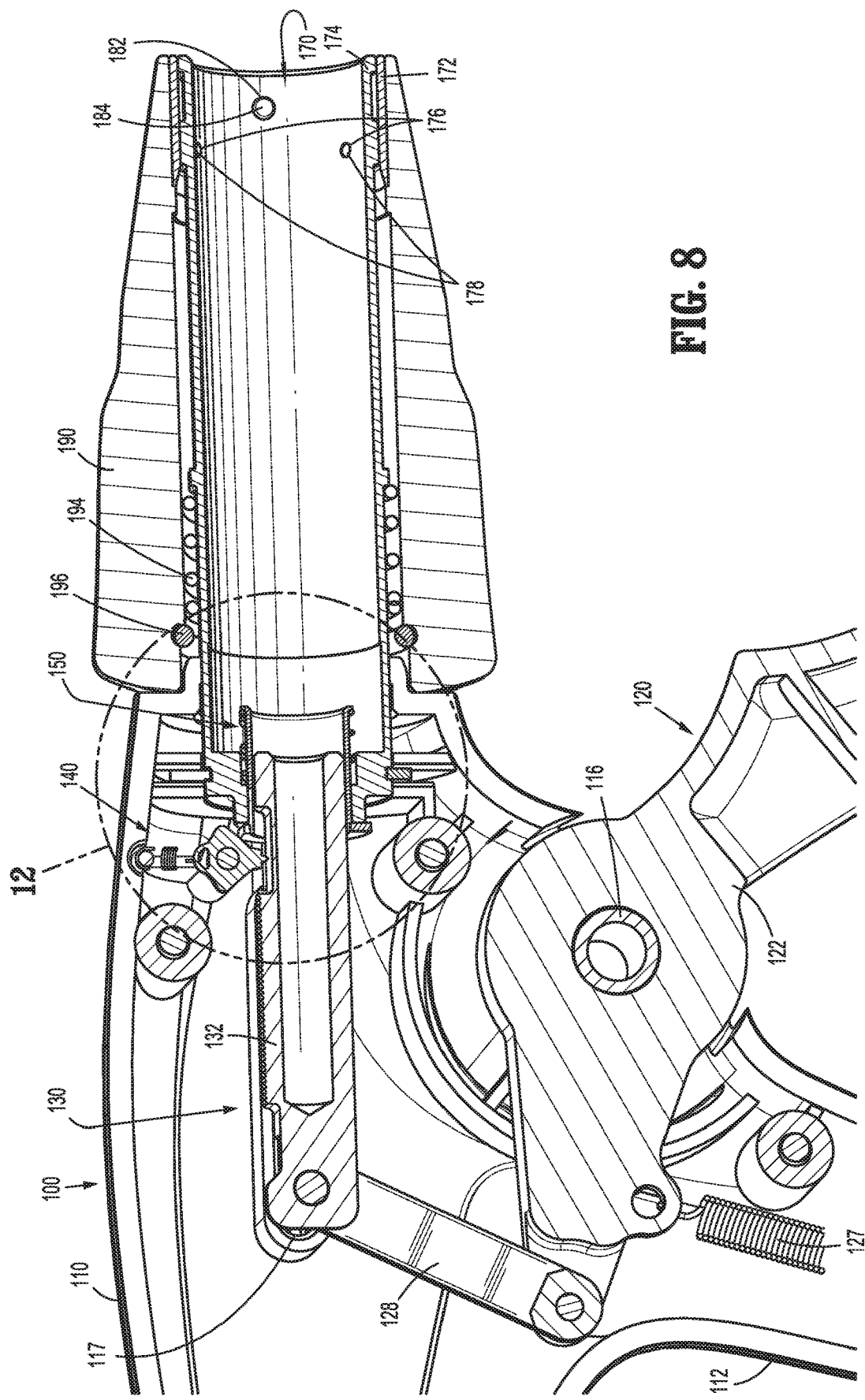
FIG. 8 is a longitudinal, cross-sectional view of handle assembly of FIG. 1.
Figure 9:
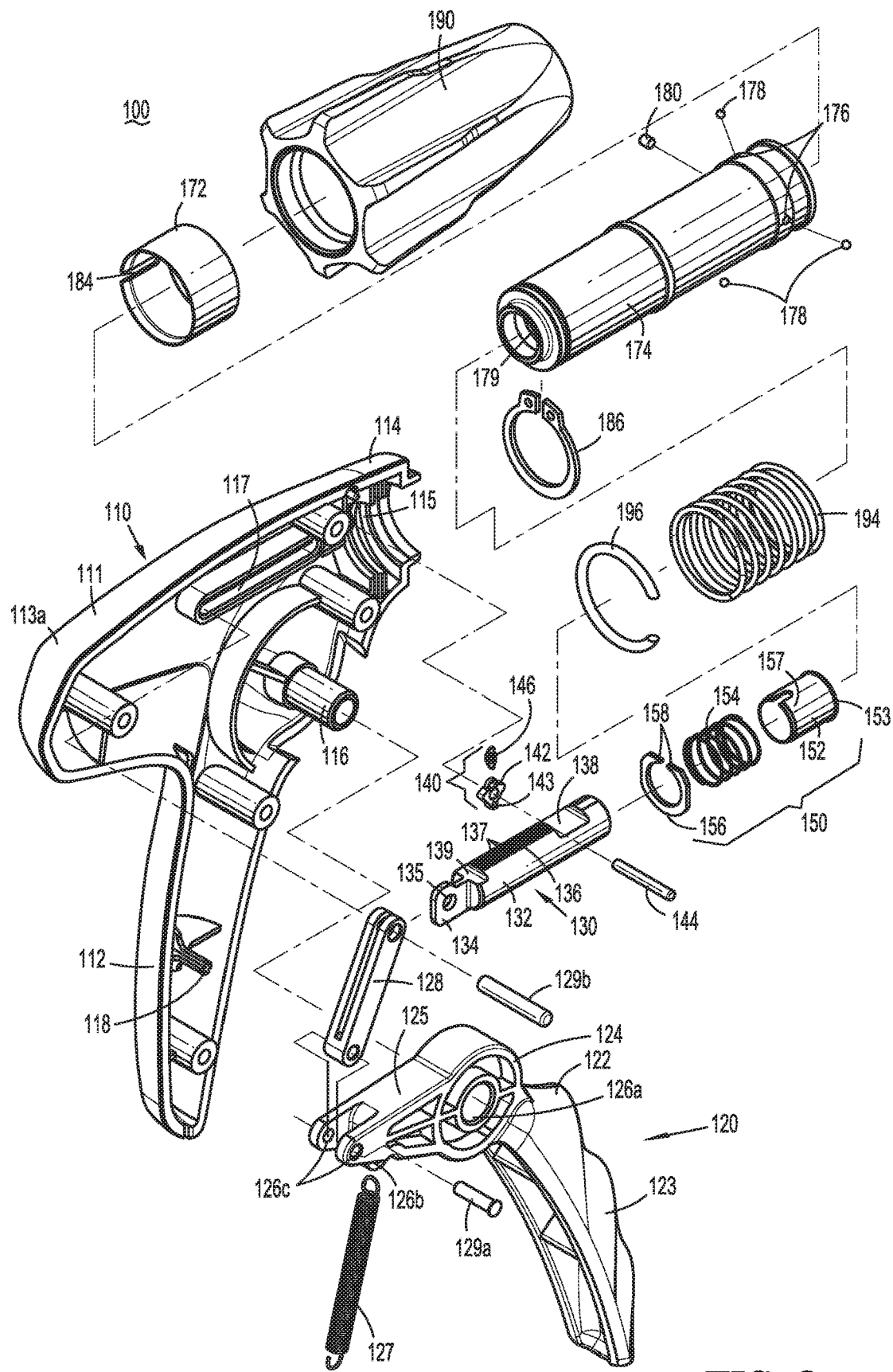
FIG. 9 is an exploded view of the handle assembly of FIG. 1.
Figure 10:
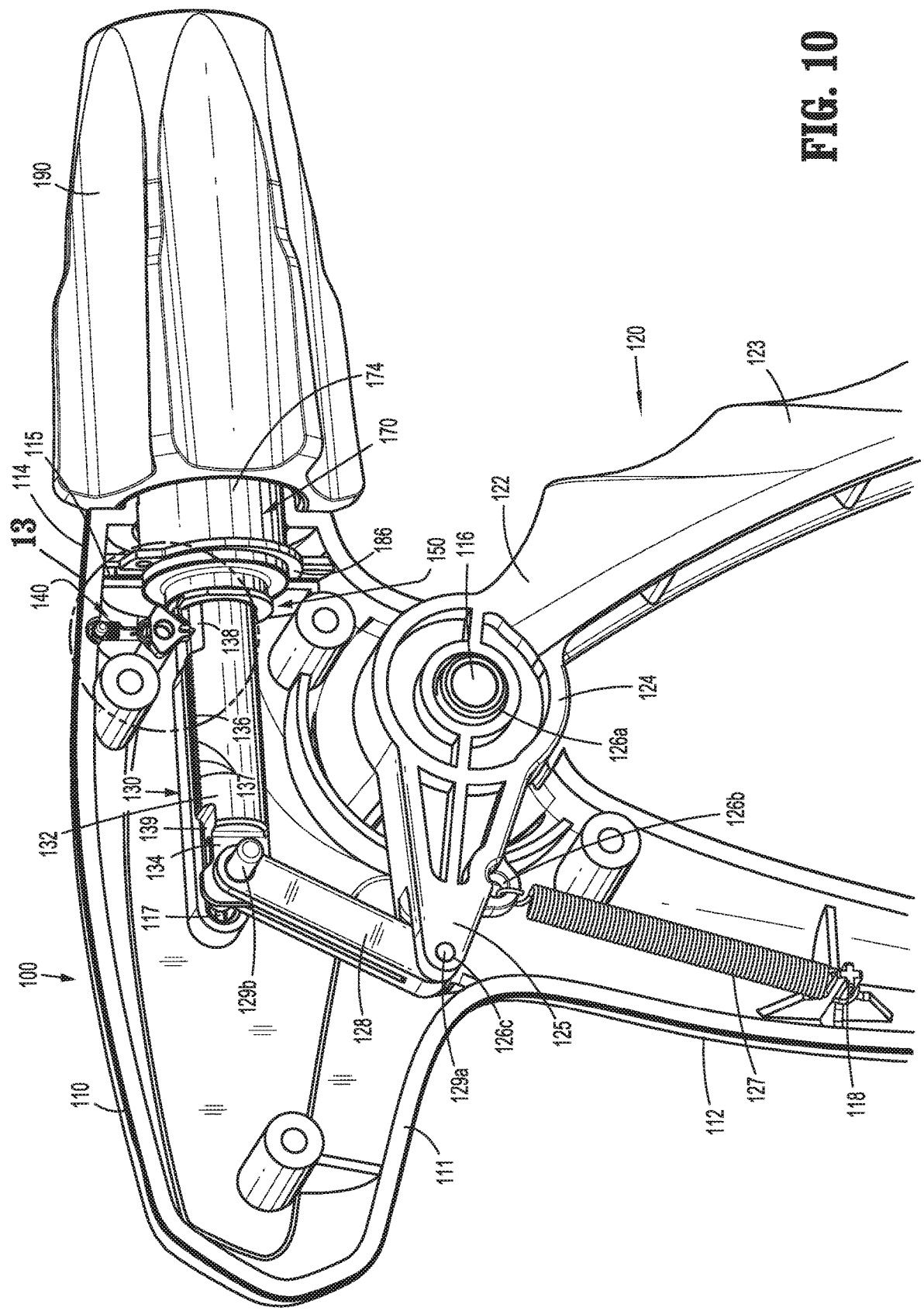
FIG. 10 is a perspective view of the handle assembly of FIG. 1 with a portion of the housing removed to illustrate the internal components therein.

Referring additionally to FIGS. 3-5, handle assembly 100 includes a receiver assembly 170 configured to receive proximal hub 210 of endoscopic assembly 200 and enable releasable engagement of endoscopic assembly 200 with handle assembly 100. Receiver assembly 170 includes an outer collar 172 and an inner tubular member 174. Inner tubular member 174 defines an interior diameter slightly larger than an exterior diameter of proximal hub 210 of endoscopic assembly 200 to enable slidable insertion of proximal hub 210 into inner tubular member 174 without significant play therebetween. Inner tubular member 174 further includes a plurality of apertures 176 defined therethrough and positioned circumferentially about inner tubular member 174. Apertures 176 define reduced interior openings 177a as compared to the exterior openings 177b thereof. A ball bearing 178 is disposed within each of the apertures 176. Although a portion of each ball bearing 178 protrudes inwardly through the reduced interior opening 177a of its respective aperture 176, the reduced interior openings 177a inhibit ball bearings 178 from passing entirely therethrough. Outer collar 172 is positioned so as to block the exterior openings 177b of apertures, thereby retaining ball bearings 178 within apertures 176 between outer collar 172 and the reduced interior openings 177a (except for the portions of ball bearings 178 extending through the reduced interior openings 177a).

A pin 180 extends through a pin aperture 182 defined within inner tubular member 174 and at least partially through a pin slot 184 defined within outer collar 172. Pin 180 extends at least partially into the interior of inner tubular member 174 and, as detailed below, is configured to facilitate alignment of endoscopic assembly 200 upon insertion of endoscopic assembly 200 into handle assembly 100. Pin 180 is further configured to retain outer collar 172 and inner tubular member 174 in fixed rotational orientation relative to one another. Outer collar 172 is engaged with rotation knob 190 of handle assembly 100 in fixed rotational orientation such that, with pin 180 rotatably coupling outer collar 172 and inner tubular member 174, rotation of rotation knob 190 can be effected to similarly rotate receiver assembly 170. Rotation knob 190 includes an alignment indicator 192 disposed thereon that is aligned with pin 180 to enable alignment of endoscopic assembly 200 with receiver assembly 170 without the need to directly view the position of pin 180.

With reference to FIGS. 1, 2, 6 and 7, in order to engage endoscopic assembly 200 with handle assembly 100, endoscopic assembly 200 is oriented such that longitudinally-extending slot 212 thereof is aligned with pin 180 of receiver assembly 170. As noted above, rather than having to view pin 180 directly, alignment of longitudinally-extending slot 212 and pin 180 can be achieved via aligning longitudinally-extending slot 212 with alignment indicator 192 of rotation knob 190 of handle assembly 100. Once alignment has been achieved, proximal hub 210 of endoscopic assembly 200 is slid proximally into inner tubular member 174 of receiver assembly 170. Alignment of longitudinally-extending slot 212 and pin 180 ensures that, upon proximal sliding of proximal hub 210 into inner tubular member 174, pin 180 is translated through longitudinally-extending slot 212.

As proximal hub 210 is slid proximally into inner tubular member 174, ball bearings 178 apply radially-inward force on the exterior of proximal hub 210 causing proximal hub 210, outer collar 172, inner tubular member 174, and/or ball bearings 178 to move or flex to accommodate proximal hub 210 between ball bearings 178. Ball bearings 178 are permitted to rotate within apertures 176 as proximal hub 210 is slid proximally into inner tubular member 174, reducing friction and permitting relatively easy sliding of proximal hub 210 into inner tubular member 174. Upon full insertion of proximal hub 210 into inner tubular member 174, e.g., upon pin 180 reaching the closed, distal end of longitudinally-extending slot 212, ball bearings 178 are moved into position about annular groove 214. As a result of the radially-inward force imparted by ball bearings 178, once the fully inserted position has been achieved, ball bearings 178 are urged into annular groove 214 to thereby releasably lock proximal hub 210 of endoscopic assembly 200 in engagement within receiver assembly 170 of handle assembly 100. The operable coupling of endoscopic assembly 200 with handle assembly 100 to enable operation thereof to perform one or more surgical tasks depends upon the type of endoscopic assembly 200 engaged with handle assembly 100 and will be detailed below with respect to exemplary endoscopic assemblies 300 (FIG. 15) and 400 (FIG. 22).

In order to remove endoscopic assembly 200 from handle assembly 100, endoscopic assembly 200 is pulled distally relative to handle assembly 100 under sufficient urging so as to dislodge ball bearings 178 from annular groove 214, thus permitting proximal hub 210 of endoscopic assembly 200 to be slid distally out of receiver assembly 170 of handle assembly 100.

Referring to FIGS. 1, 2, and 8-10, handle assembly 100 generally includes a housing 110, a trigger assembly 120 pivotably coupled to housing 110, a ratcheting drive assembly 130 operably coupled to trigger assembly 120, a bypass assembly 150 operably coupled to ratcheting drive assembly 130, receiver assembly 170 which extends distally from housing 110, and rotation knob 190 which is operably disposed about receiver assembly 170.

Housing 110 defines a body portion 111 and a fixed handle portion 112 extending downwardly from body portion 111. Housing 110 is formed from first and second housing components 113a, 113b secured to one another via pin-post engagement, although first and second housing components 113a, 113b may alternatively be secured in any other suitable manner, e.g., ultrasonic welding, gluing, other mechanical engagement, etc. Housing 110 is configured to house the internal working components of handle assembly 100. Body portion 111 includes a distal nose 114 defining an annular slot 115 on the interior thereof. More specifically, first and second housing components 113a, 113b each define a semi-annular slot portion such that, when first and second housing components 113a, 113b cooperate to form housing 110, annular slot 115 is formed. Receiver assembly 170 of handle assembly 100 includes a retention clip 186 disposed about the proximal end of inner tubular member 174 thereof. Retention clip 186 is captured within annular slot 115 defined within distal nose 114 of housing 110, e.g., upon engagement of first and second housing components 113a, 113b with one another. Retention clip 186 is captured within annular slot 115 to rotatably engage receiver assembly 170 with housing 110. Rotation knob 190 of handle assembly 100 is operably engaged about receiver assembly 170, e.g., via outer collar 172, biasing member 194, and elastomeric C-ring 196, in fixed rotational orientation relative thereto such that rotation of rotation knob 190 relative to housing 110 effects similar rotation of receiver assembly 170 relative to housing 110. Thus, with endoscopic assembly 200 engaged within receiver assembly 170, rotation knob 190 may be rotated relative to housing 100 to similarly rotate endoscopic assembly 200 relative to housing 110.

Body portion 111 of housing 110 further incudes an internal pivot post 116 extending transversely between housing components 113a, 113b and a longitudinally-extending guide track 117 defined within one or both of housing components 113a, 113b, the importance of each of which is detailed below. Fixed handle portion 112 of housing 110 is configured to facilitate grasping of handle assembly 100 and manipulation thereof and is monolithically formed with body portion 111, although other configurations are also contemplated.

Figure 11:
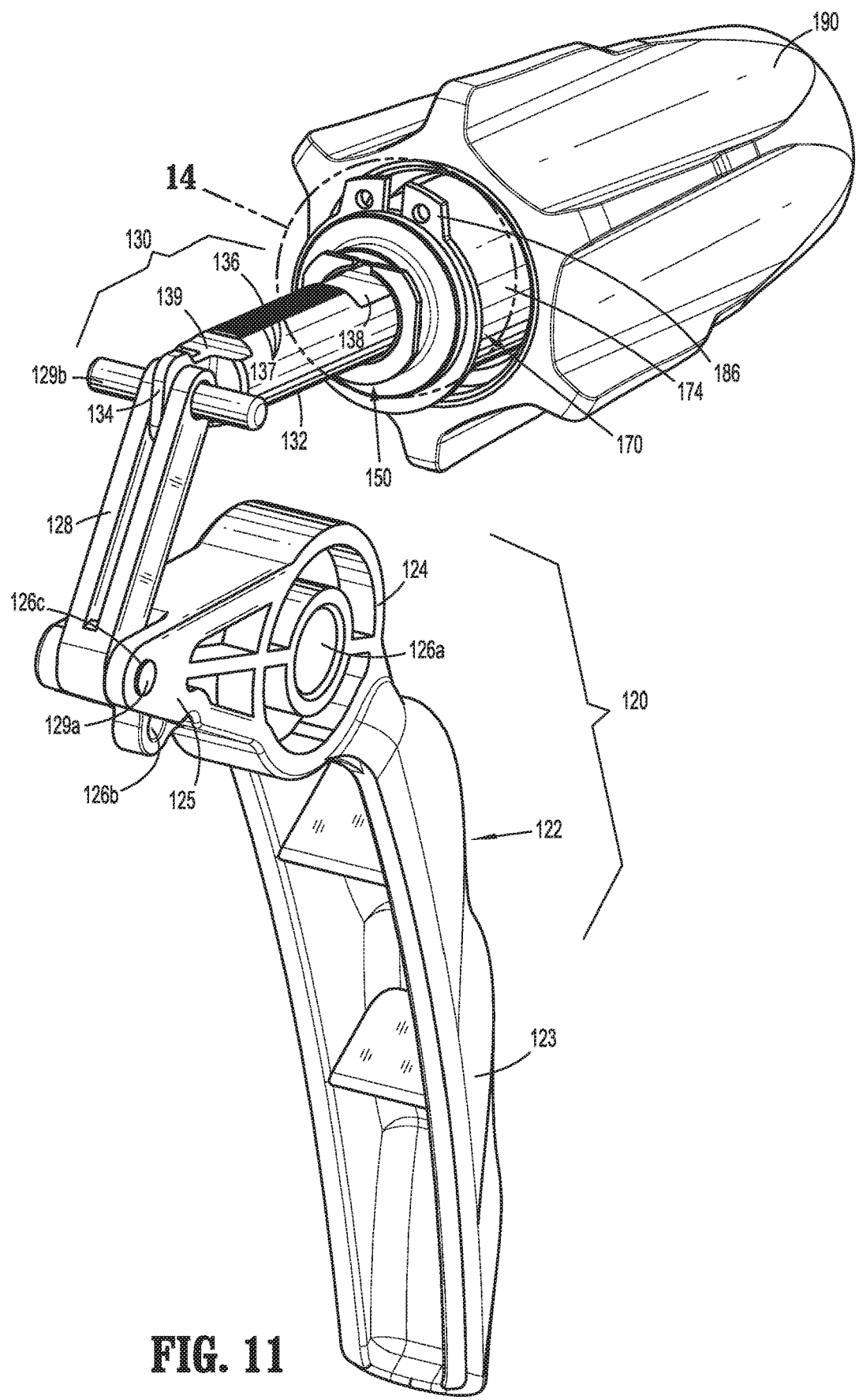
FIG. 11 is a perspective view of the internal assemblies of the handle assembly of FIG. 1.

With additional reference to FIG. 11, trigger assembly 120 generally includes a trigger 122, a biasing member 127, and a linkage 128. Trigger 122 includes a grasping portion 123, an intermediate pivot portion 124, and a proximal extension portion 125. Grasping portion 123 of trigger 122 extend downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126a that is configured to receive pivot post 116 of housing 110 so as to enable pivoting of trigger 122 about pivot post 116 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension portion 125 of trigger 122 of trigger assembly 120 is disposed on an opposite side of intermediate pivot portion 124 and, thus, pivot post 116, as compared to grasping portion 123 of trigger 122. As such, pivoting of grasping portion 123 proximally, e.g., towards the actuated position, urges proximal extension portion 125 distally. Proximal extension portion 125 includes a first aperture 126b configured to receive a first end of biasing member 127, and a pair of second apertures 126c configured to receive a first pin 129a for pivotably coupling the proximal end of linkage 128 and proximal extension portion 125 of trigger 122 with each other. The second end of biasing member 127 is engaged about an arm 118 extending transversely within fixed handle portion 112. Biasing member 127 is disposed in an at-rest condition in the un-actuated position of grasping portion 123 of trigger 122. Pivoting of grasping portion 123 towards the actuated position elongates biasing member 127 storing energy therein such that, upon release of grasping portion 123, grasping portion 123 is returned towards the un-actuated position under the bias of biasing member 127. Although illustrated as an extension coil spring, biasing member 127 may define any suitable configuration for biasing grasping portion 123 of trigger 122 towards the un-actuated position.

As noted above, linkage 128 is coupled at its proximal end to proximal extension portion 125 of trigger 122 via first pin 129a. Linkage 128 is also pivotably coupled, at its distal end, to proximal extension 134 of drive bar 132 of ratcheting drive assembly 130 via a second pin 129b. Second pin 129b extends outwardly from either or both sides of proximal extension 134 of drive bar 132 and is received within the longitudinally-extending guide track(s) 117 defined within housing component 113a and/or housing component 113b. As a result of this configuration, pivoting of grasping portion 123 towards the actuated position urges proximal extension portion 125 distally which, in turn, urges linkage 128 distally such that second pin 129b is translated distally through longitudinally-extending guide track(s) 117.

Continuing with reference to FIGS. 1, 2, and 8-11, ratcheting drive assembly 130 of handle assembly 100 includes a drive bar 132 and a pawl assembly 140. Drive bar 132 includes a proximal extension 134, a ratchet rack 136, and distal and proximal recesses 138, 139, respectively. Proximal extension 134 is disposed at the proximal end of the drive bar 132 and defines an aperture 135 configured to receive second pin 129b of trigger assembly 120 so as to pivotably couple the distal end of linkage 128 and drive bar 132 with one another, as noted above. As such, upon pivoting of grasping portion 123 towards the actuated position to urge second pin 129b distally through longitudinally-extending guide track(s) 117, drive bar 132 is translated distally through body portion 111 of housing 110. Ratchet rack 136 of drive bar 132 defines a plurality of teeth 137 and extends longitudinally along drive bar 132 on an upper surface thereof. Distal and proximal recesses 138, 139 are defined by cut-outs formed in drive bar 132 and are positioned distally adjacent ratchet rack 136 and proximally adjacent ratchet rack 136, respectively.

Figure 12:
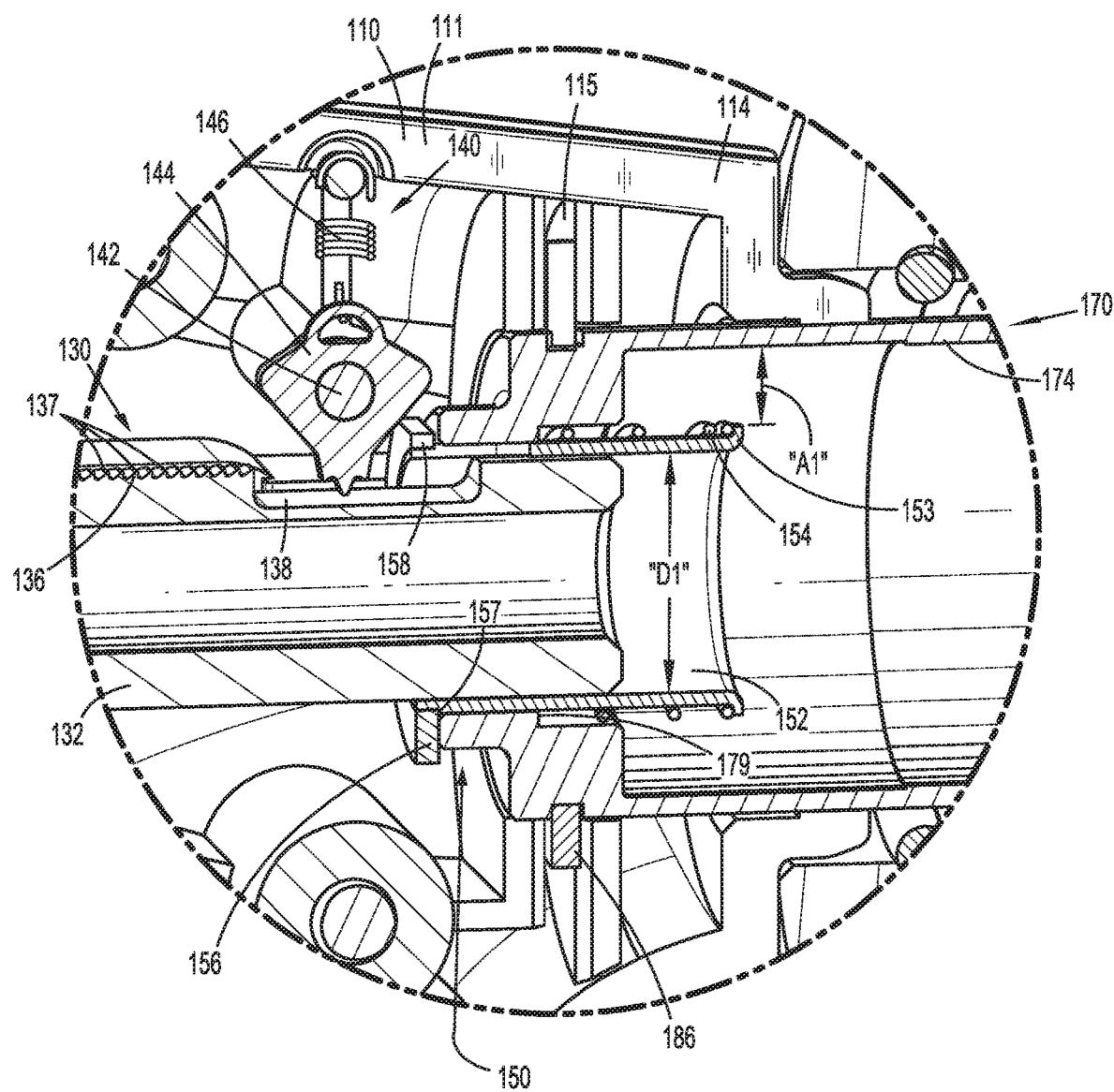
FIG. 12 is an enlarged, longitudinal, cross-sectional view of the area of detail indicated as "12" in FIG. 8.
Figure 13:
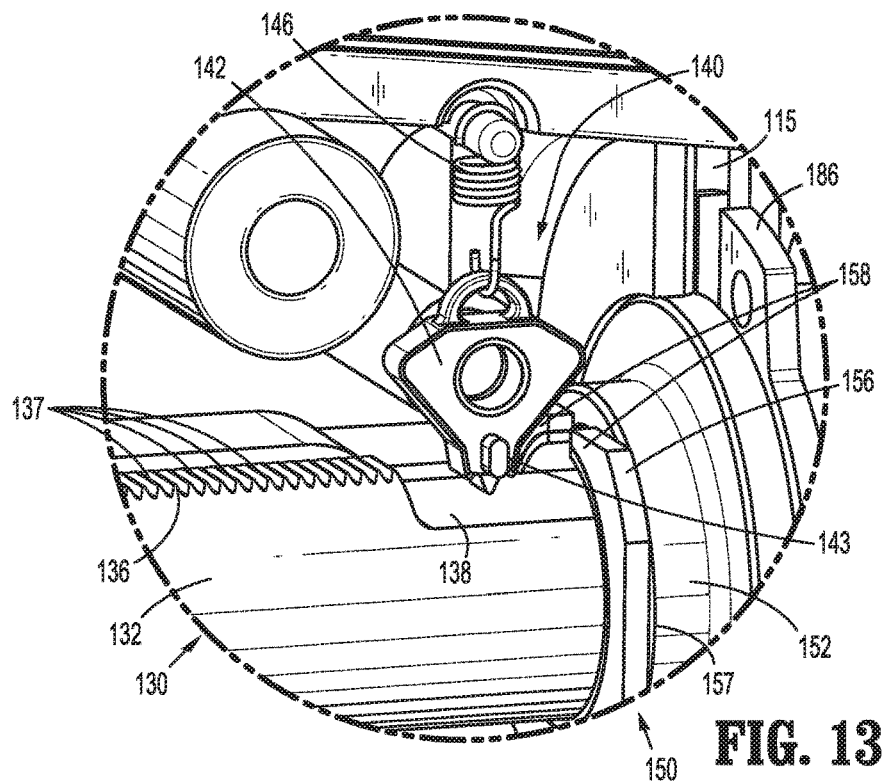
FIG. 13 is an enlarged, perspective view of the area of detail indicated as "13" in FIG. 10.
Figure 14:
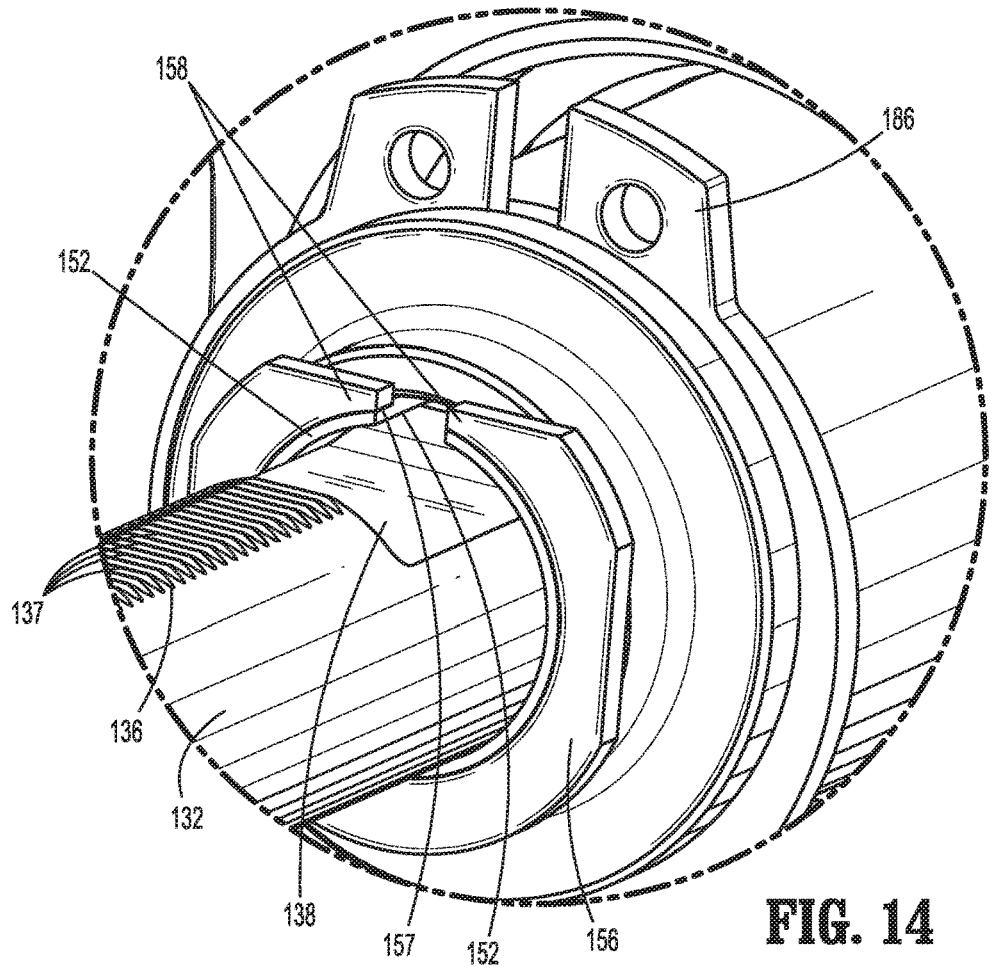
FIG. 14 is an enlarged, perspective view of the area of detail indicated as "14" in FIG. 11.
Figure 19:
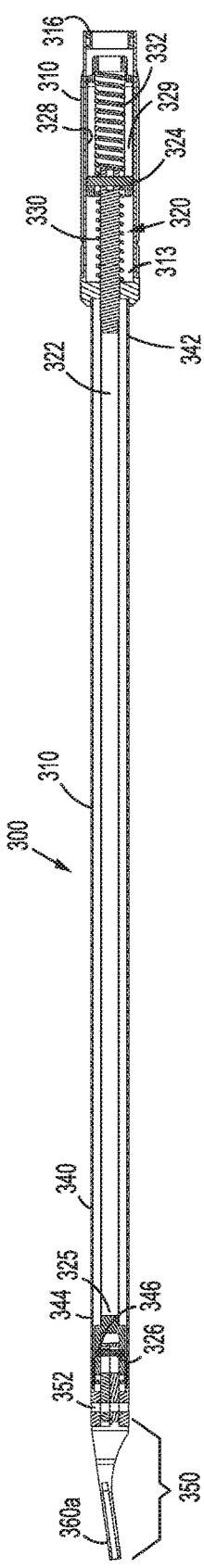
FIG. 19 is a longitudinal, cross-sectional view of the endoscopic assembly of FIG. 15.
Figure 20:
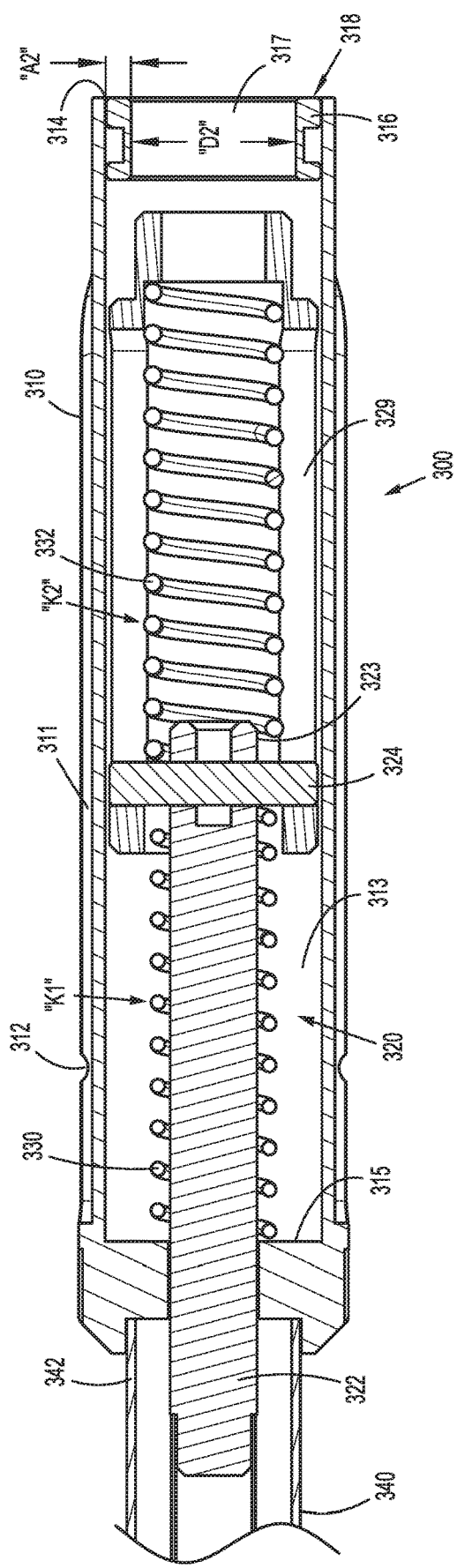
FIG. 20 is an enlarged, longitudinal, cross-sectional view of the proximal portion of the endoscopic assembly of FIG. 15.

Referring also to FIG. 12, pawl assembly 140 of ratcheting drive assembly 130 includes a ratchet pawl 142, a pawl pin 144, and a pawl biasing member 146. Ratchet pawl 142 is pivotably coupled to body portion 111 of housing 110 by pawl pin 144 so as to enable operable engagement of ratchet pawl 142 with ratchet rack 136 when an endoscopic assembly 200 that uses the ratcheting function is connected to handle assembly 100, and to enable pivoting of ratchet pawl 142 to a bypass position when a endoscopic assembly 200 that does not use the ratcheting function is connected to handle assembly 100. Ratchet pawl 142 further includes a pair of outwardly-extending tabs 143 extending transversely from either side thereof, the importance of which are detailed below.

Pawl biasing member 146 of pawl assembly 140 is coupled between ratchet pawl 142 and body portion 111 of housing 110 so as to bias ratchet pawl 142 towards a use position and away from the bypass position. In the use position, ratchet pawl 142 is oriented to operably engage ratchet rack 136 upon distal advancement of drive bar 132. However, in the proximal-most position of drive bar 132, corresponding to the un-actuated position of trigger 122, ratchet pawl 142 is disposed at least partially within distal recess 138 of drive bar 132. Accordingly, at least initially, ratchet pawl 142 is disengaged from ratchet rack 136.

With reference to FIGS. 8-14, bypass assembly 150 is operably positioned between pawl assembly 140 and receiver assembly 170 and is configured, in response to engagement of handle assembly 100 with an endoscopic assembly 200 that does not use the ratcheting function, to pivot ratchet pawl 142 to the bypass position, thereby inhibiting ratcheting upon advancement of drive bar 132. When an endoscopic assembly 200 that uses the ratcheting function is connected to handle assembly 100, bypass assembly 150 remains idle such that ratchet pawl 142 remains in the use position to enable ratcheting of ratchet pawl 142 along ratchet rack 136 upon advancement of drive bar 132.

Bypass assembly 150 includes a sleeve 152, a biasing member 154, and a camming clip 156. Sleeve 152 extends into the proximal end of inner tubular member 174 of receiver assembly 170 and is disposed about the distal end of drive bar 132 of drive assembly 130 in slidable relation relative to both inner tubular member 174 and drive bar 132. Biasing member 154 is disposed within inner tubular member 174 of receiver assembly 170 and about sleeve 152. More specifically, biasing member 154 is retained about sleeve 152 between a distal rim 153 of sleeve 152 and an annular shoulder 179 defined within the interior of inner tubular member 174 at the proximal end thereof. As a result of this configuration, biasing member 154 biases sleeve 152 proximally into the interior of inner tubular member 174. Distal rim 153 of sleeve 152 is radially-spaced rom the interior wall defining inner tubular member 174 so as to define an annular spacing "A1" therebetween. Sleeve 152 further defines an internal diameter "D1."

Camming clip 156 of bypass assembly 150 is engaged within an annular groove 157 defined about the exterior of sleeve 152 towards the proximal end thereof. Camming clip 156 is sufficiently dimensioned so as to inhibit passage into the interior of inner tubular member 174 and, thus, inhibits sleeve 152 from fully entering inner tubular member 174 under the bias of biasing member 154. Camming clip 156 further include a pair of opposed, inwardly extending fingers 158 at the free ends thereof. Fingers 158 are positioned such that, upon sufficient proximal urging of sleeve 152 against the bias of biasing member 154, fingers 158 contact respective tabs 143 of ratchet pawl 142. Thus, upon further proximal movement of sleeve 152, fingers 158 urge respective tabs 143 proximally, ultimately such that ratchet pawl 142 is urged to rotate about pawl pin 144 and against the bias of pawl biasing member 146 from the use position to the bypass position.

Turning to FIGS. 15-21, and endoscopic assembly 300 provided in accordance with the present disclosure and configured for use with handle assembly 100 is shown. Endoscopic assembly 300 is configured for non-ratcheting use and, thus, upon engagement of endoscopic assembly 300 with handle assembly 100, as detailed below, ratchet pawl 142 is pivoted to and retained in the bypass position, thus enabling such non-ratcheting use. Endoscopic assembly 300 generally includes a proximal hub 310, an inner drive assembly 320 disposed within and extending through proximal hub 310, an elongated shaft 340 extending distally from proximal hub 310, and an end effector assembly 350 including a pair of jaw members 360a, 360b disposed at the distal end of elongated shaft 340. Endoscopic assembly 300 is configured to grasp and/or manipulate tissue, retrieve a surgical clip, and to close, fire, or form the surgical clip about tissue. It is contemplated that endoscopic assembly 300 be configured to close, fire or form surgical clips similar to those shown and described in U.S. Pat. No. 4,834,096, the entire contents of which are incorporated herein by reference.

With additional reference to FIGS. 1, 2, 6, and 7, proximal hub 310 of endoscopic assembly 300 defines a generally tubular configuration and an exterior diameter slightly smaller than that of inner tubular member 174 of receiver assembly 170 of handle assembly 100 to enable slidable insertion of proximal hub 310 into inner tubular member 174 without significant play therebetween. Proximal hub 310 further includes features similar to those detailed above with respect to endoscopic assembly 200 so as to enable engagement of proximal hub 310 within receiver assembly 170 of handle assembly 100 in a similar fashion. More specifically, proximal hub 310 a longitudinally-extending slot 311 configured to receive pin 180 of receiver assembly 170 to ensure proper alignment of endoscopic assembly 300 relative to handle assembly 100, and an annular groove 312 configured to receive at least a portion of each ball bearing 178 to releasably lock proximal hub 310 of endoscopic assembly 300 in engagement within receiver assembly 170 of handle assembly 100.

Referring again to FIGS. 15-21, proximal hub 310 of endoscopic assembly 300 further defines an internal bore 313 having an open proximal end 314 and a reduced-diameter distal opening as compared to the diameter of bore 313 so as to define a shoulder 315 therebetween. A ferrule 316 is seated within the open proximal end of proximal hub 310 and secured therein in any suitable fashion, e.g., welding, gluing, press-fitting, mechanical engagement, etc.

Ferrule 316 of proximal hub 310 defines an aperture 317 extending longitudinally therethrough and a proximally-facing surface 318 surrounding aperture 317 such that proximally-facing surface 318 defines a ring-shaped configuration. Aperture 317 is disposed in communication with the interior of proximal hub 310 so as to provide access to inner drive assembly 320, as detailed below, and defines a diameter "D2" that is sufficiently large so as to permit slidable insertion of drive bar 132 of ratcheting drive assembly 130 of handle assembly 100 therethrough. However, diameter "D2" of aperture 317 is smaller than internal diameter "D1" of sleeve 152. Proximally-facing surface 318 of ferrule 316 defines an annular width "A2" that is larger than the annular spacing "A1" defined between distal rim 153 of sleeve 152 and the interior wall defining inner tubular member 174. As a result of diameter "D2" being smaller than diameter "D1" and annular width "A2" being larger than annular spacing "A1," proximal hub 310 is inhibited from passing into the interior of sleeve 152 and is likewise inhibited from passing about the exterior of sleeve 152. Rather, upon proximal urging of proximal hub 310 of endoscopic assembly 300 into inner tubular member 174 of receiver assembly 170 of handle assembly 100, e.g., to engage endoscopic assembly 300 with handle assembly 100, proximally-facing surface 318 of ferrule 316 eventually contacts distal rim 153 of sleeve 152 such that further proximal urging of proximal hub 310 into inner tubular member 174 urges sleeve 152 proximally against the bias of biasing member 154.

Figure 21:
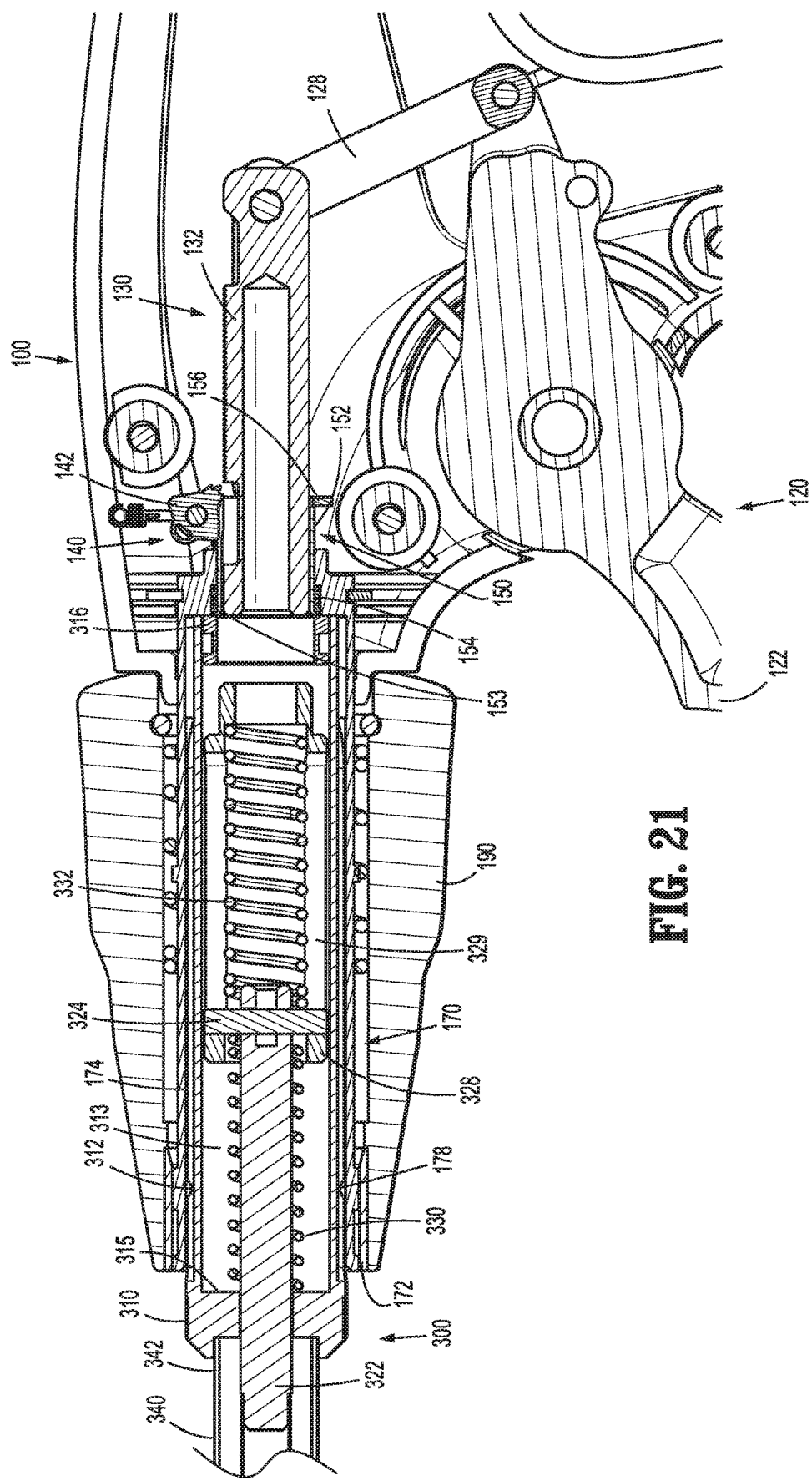
FIG. 21 is an enlarged, longitudinal, cross-sectional view illustrating the operable engagement between the handle assembly of FIG. 1 and the endoscopic assembly of FIG. 15.
Figure 28:
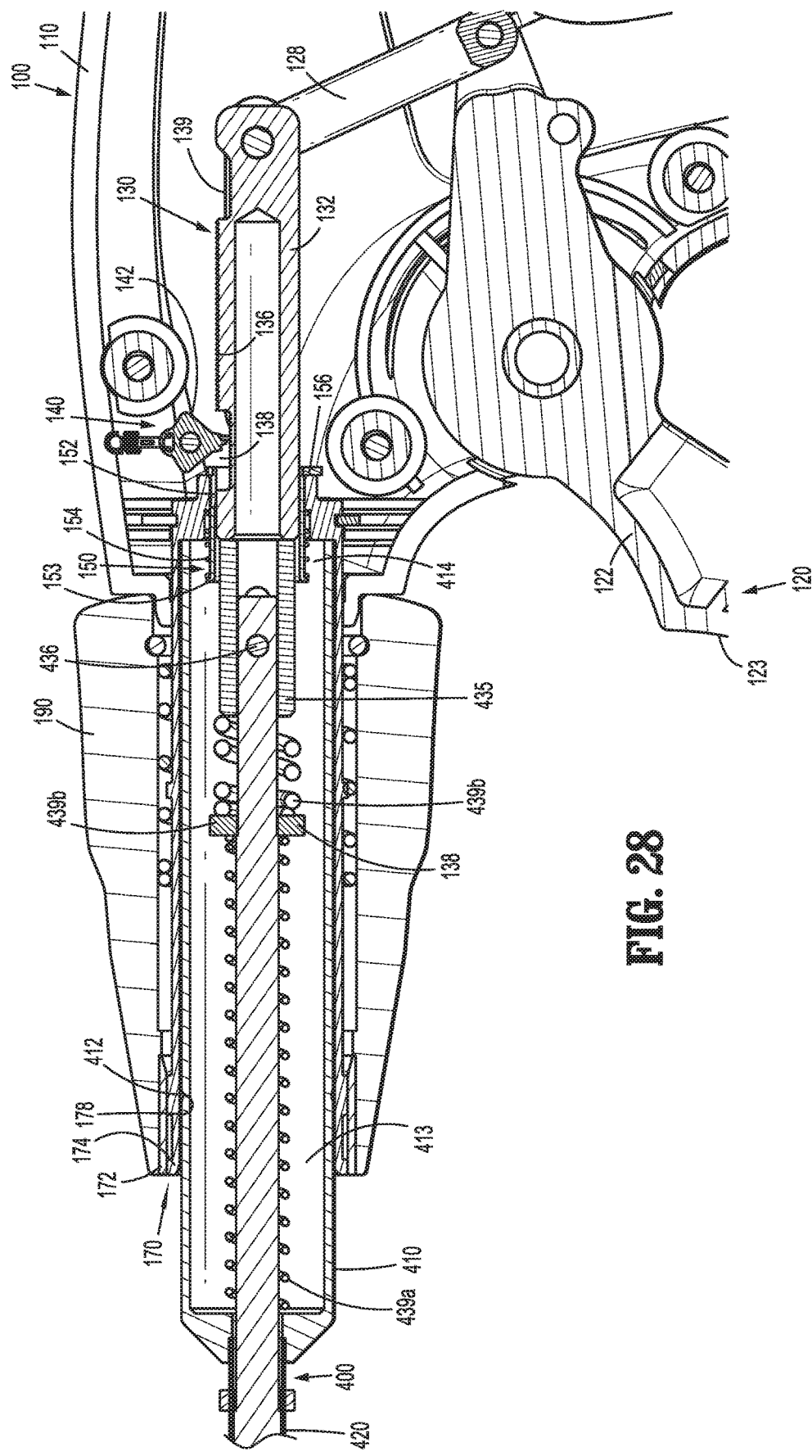
FIG. 28 is an enlarged, longitudinal, cross-sectional view illustrating the operable engagement between the handle assembly of FIG. 1 and the endoscopic assembly of FIG. 22.

As noted above, endoscopic assembly 300 is configured for non-ratcheting use. Accordingly, the above-detailed configuration regarding the relative dimensions of the components of proximal hub 310 and those of bypass assembly 150 ensures that proximal hub 310 urges ratchet pawl 142 from the use position to the bypass position upon engagement of endoscopic assembly 300 with handle assembly 100, thus disabling the ratcheting components of ratcheting drive assembly 130. More specifically, with pin 180 received within longitudinally-extending slot 311 and proximal hub 310 sliding proximally into inner tubular member 174 of receiver assembly 170, but prior to engagement of ball bearings 178 within annular groove 312, proximally-facing surface 318 of ferrule 316 contacts distal rim 153 of sleeve 152 and urges sleeve 152 proximally such that fingers 158 of camming clip 156 urge tabs 143 of ratchet pawl 142 proximally to thereby rotate ratchet pawl 142 about pawl pin 144 from the use position towards the bypass position. Accordingly, upon reaching the engaged position of proximal hub 310 within inner tubular member 174, e.g., upon engagement of ball bearings 178 within annular groove 312, as shown in FIG. 21, ferrule 316 has urged sleeve 152 to a proximal-most position wherein ratchet pawl 142 is pivoted to and retained in the bypass position. Thus, when endoscopic assembly 300 is engaged with handle assembly 100, ratcheting of ratcheting drive assembly 130 is disabled.

Referring still to FIGS. 15-21, inner drive assembly 320 of endoscopic assembly 300 includes an inner shaft 322 slidably disposed within both proximal hub 310 and elongated shaft 340 of endoscopic assembly 300. Inner shaft 322 includes a proximal end 323 supporting a transverse pin 324 disposed within bore 313 of proximal hub 310, and a distal end 325 supporting a cam pin 326 disposed towards the distal end 344 of elongated shaft 340. As detailed below, cam pin 326 is disposed within cam slots (not shown) of jaw members 360a, 360b of end effector assembly 350 to enable pivoting of jaw members 360a, 360b between open and closed positions in response to translation of inner shaft 322 through elongated shaft 340.

Inner drive assembly 320 further includes a plunger 328 and first and second biasing members 330, 332, respectively. Plunger 328 is slidably disposed within bore 313 of proximal hub 310 and is retained therein between shoulder 315 and ferrule 316. Plunger 328 defines an internal cavity 329 within which transverse pin 324 of proximal end 323 of inner shaft 322 is slidably confined.

First biasing member 330 of inner drive assembly 320 is disposed within internal bore 313 of proximal hub 310 and interposed between shoulder 315 of proximal hub 310 and transverse pin 324 of inner shaft 322. First biasing member 330 has a first spring constant "K1" which is less than a second spring constant "K2" of second biasing member 332, the importance of which is detailed below. Second biasing member 332 is disposed within cavity 329 of plunger 328 and is interdisposed between transverse pin 324 of inner shaft 322 and the proximal end of plunger 328. As detailed below, first and second biasing members 330, 332, respectively, facilitate appropriate translation of inner shaft 322 through proximal hub 310 and elongated shaft 340 to open and close jaw members 340a, 340b, and to enable full actuation of trigger 122 (FIG. 1), as detailed below.

Elongated shaft 340 of endoscopic assembly 300 defines a generally tubular configuration and extends between and interconnects proximal hub 310 and end effector assembly 350. More specifically, the proximal end 342 of elongated shaft 340 is secured to proximal hub 310, while the distal end 344 of elongated shaft 340 supports a clevis 346 configured to pivotably engage jaw members 360a, 360b of end effector assembly 350 at distal end 344 of elongated shaft 340 via a pivot pin 352.

End effector assembly 350, as noted above, includes first and second jaw members 360a, 360b. Jaw members 360a, 360b are pivotably engaged to one another and clevis 346 via pivot pin 352 so as to permit pivoting of jaw members 360a, 360b relative to one another and elongated shaft 340 between an open position and a closed position. Each jaw member 360a, 360b includes a respective proximal end 361a, 361b and a respective distal end 362a, 362b. The proximal end 361a, 361b of each jaw member 360a, 360b defines the cam slots (not shown) that are configured to receive cam pin 326 of inner shaft 322 such that translation of inner shaft 322 pivots jaw members 360a, 360b between the open and closed positions. The distal ends 362a, 362b of jaw members 360a, 360b are configured to receive and close, fire or form a surgical clip, e.g., a surgical clip similar to those shown and described in U.S. Pat. No. 4,834,096, previously incorporated herein by reference.

The use of handle assembly 100 in conjunction with endoscopic assembly 300 is now detailed with reference to FIGS. 8-21. Initially, endoscopic assembly 300 is engaged with handle assembly 100, as detailed above. Such engagement of endoscopic assembly 300 with handle assembly 100, as also detailed above, effects pivoting of ratchet pawl 142 to and retention of ratchet pawl 142 in the bypass position. Once endoscopic assembly 300 and handle assembly 100 are engaged with ratchet pawl 142 in the bypass position, handle assembly 100 and endoscopic assembly 300 are together ready for use.

In use, trigger 122 is initially disposed in the un-actuated position under the bias of biasing member 127. With trigger 122 disposed in the un-actuated position, drive bar 132 is disposed in a proximal-most position. Further, inner shaft 322 is disposed in a proximal-most position under the bias of first and second biasing members 330, 332. Thus, jaw members 360a, 360b, initially, are disposed in the open position. With jaw members 360a, 360b disposed in the open position, a new, unformed or open surgical clip (not shown) may be located or loaded within the distal ends 362a, 362b of jaw members 360a, 360b. Jaw members 360a, 360b of end effector assembly 350 may be used to retrieve or pick-up a surgical clip from a clip holder (not shown), the surgical clip may be manually loaded by the user, end effector assembly 350 may be pre-loaded by the manufacturer, or the surgical clip may be placed between jaw members 360a, 360b in any other suitable fashion.

In or to close, fire, or form the surgical clip loaded between jaw members 360a, 360b, trigger 122 is urged from the un-actuated position to the actuated position. More specifically, grasping portion 123 of trigger 122 is pivoted towards fixed handle portion 112 of housing 110 to urge linkage 128 distally which, in turn, urges drive bar 132 distally through housing 110, receiver assembly 170, and into bore 313 of proximal hub 310 of endoscopic assembly 300. As trigger 122 is pivoted further towards the actuated position, drive bar 132 eventually contacts plunger 328 of drive assembly 320 of endoscopic assembly 300. Due to first spring constant "K1" of first biasing member 330 being less than second spring constant "K2" of second biasing member 332, as drive bar 132 is initially urged into plunger 328, plunger 328 and inner shaft 322 translate together distally such that first biasing member 330 is compressed while second biasing member 332 remains substantially un-compressed.

As inner shaft 322 is translated distally, cam pin 326 is translated through the cam slots of jaw members 360a, 360b to pivot jaw members 360a, 360b towards the closed position to close and/or form the surgical clip (not shown) loaded within end effector assembly 350. Cam pin 326 is advanced distally until cam pin 326 reaches an end of the cam slots of jaw members 360a, 360b and/or until jaw members 360a, 360b are fully approximated against one another or fully closed on the surgical clip. As can be appreciated, depending upon the particular endoscopic assembly used, the configuration of the surgical clip being formed, and/or other factors, the required travel distance of inner shaft 322 to fully form the surgical clip may vary. As the distance of travel for trigger 122 between the un-actuated and actuated positions does not vary, it is endoscopic assembly 300 that accounts for this variation, as detailed below.

Once jaw members 360a, 360b have been fully approximated against one another or fully closed on the surgical clip, and/or when cam pin 326 has reached the end of the cam slots of jaw members 360a, 360b, inner shaft 322 is no longer permitted to travel further distally. Thus, upon further distal urging of drive bar 132, e.g., to complete the actuation stroke of trigger 122, plunger 328 is advanced distally independently of inner shaft 322 to compress second biasing member 332. Thus, the compression of second biasing member 332 enables inner shaft 322 to remain in position while the full actuation stroke of trigger 122 is completed.

Once the surgical clip has been fully formed, trigger 122 may be released and allowed to return under bias to the un-actuated position, thereby pulling drive bar 132 back to its proximal-most position and allowing jaw members 360a, 360b to return to the open position. Thereafter, the above-detailed use may be repeated to close, fire, or form additional surgical clips. Additionally or alternatively, jaw members 360a, 360b of end effector assembly 350 may be used to grasp and/or manipulate tissue as desired prior to or after formation of one or more surgical clips.

Turning to FIGS. 22-28, another endoscopic assembly 400 provided in accordance with the present disclosure and configured for use with handle assembly 100 (FIG. 1) is shown. Endoscopic assembly 400 is configured for ratcheting use and, thus, upon engagement of endoscopic assembly 400 with handle assembly 100, as detailed below, ratchet pawl 142 remains in the use position to enable ratcheting use. Endoscopic assembly 400 generally includes a proximal hub 410, an elongated shaft 420 extending distally from proximal hub 410, a drive assembly 430 disposed within proximal hub 410 and elongated shaft 420, and a pair of jaw members 460a, 460b supported at the distal end of elongated shaft 420. Endoscopic assembly 400 is configured to close, fire, or form one or more surgical clips about tissue. More specifically, it is contemplated that endoscopic assembly 400 may be configured to close, fire or form surgical clips similar to those shown and described in U.S. Pat. No. 7,819,886 or 7,905,890, the entire contents of each of which is incorporated herein by reference.

With reference also to FIGS. 1, 2, 6, and 7, proximal hub 410 further includes features similar to those detailed above with respect to endoscopic assembly 200 so as to enable engagement of proximal hub 410 within receiver assembly 170 of handle assembly 100 in a similar fashion. More specifically, proximal hub 410 a longitudinally-extending slot 411 configured to receive pin 180 of receiver assembly 170 to ensure proper alignment of endoscopic assembly 400 relative to handle assembly 100, and an annular groove 412 configured to receive at least a portion of each ball bearing 178 to releasably lock proximal hub 410 of endoscopic assembly 400 in engagement within receiver assembly 170 of handle assembly 100.

As noted above, endoscopic assembly 400 is configured for ratcheting use and, thus, upon engagement of endoscopic assembly 400 with handle assembly 100 ratchet pawl 142 remains in the use position to enable ratcheting use. To allow such, proximal hub 410 defines a ring-shaped aperture 414 annularly disposed between the outer housing defining proximal hub 410 and plunger 435 of drive assembly 430, which is slidably disposed within proximal hub 410. This ring-shaped aperture 414 is positioned and dimensioned to receive distal rim 153 of sleeve 152 upon insertion of endoscopic assembly 400 into receiver assembly 170. Thus, upon insertion of proximal hub 410 of endoscopic assembly 400 into inner tubular member 174 of receiver assembly 170 of handle assembly 100, e.g., to engage endoscopic assembly 400 with handle assembly 100, distal rim 153 of sleeve 152 passes into proximal hub 410 through ring-shaped aperture 414 undisturbed such that sleeve 152 is maintained in its distal-most position under the bias of biasing member 154. With sleeve 152 in its distal-most position, ratchet pawl 142 remains in the use position, thus enabling ratcheting use of ratcheting drive assembly 130 of handle assembly 100.

Referring back to FIGS. 22-28, as mentioned above, endoscopic assembly 400 includes an elongated shaft 420 extending distally from proximal hub 410. Elongated shaft 420 includes a proximal end 422 secured to proximal hub 410 and a distal end 424 supporting first and second jaw members 460a, 460b.

Drive assembly 430 includes an inner shaft 431 slidably supported within the interior of elongated shaft 420 and proximal hub 410. Inner shaft 431 includes a proximal end 433 and a distal end 434. The proximal end 433 of inner shaft 431 extends into internal bore 413 of proximal hub 410 and is operably coupled to plunger 435 of drive assembly 430 via receipt of transverse pin 436 of inner shaft 431 within longitudinal slots 437 of plunger 435. Distal end 434 of inner shaft 431 is configured to transition first and second jaw members 460a, 460b from an open position to a closed position to form a surgical clip (not shown) that has been loaded into first and second jaw members 460a, 460b in response to distal translation of inner shaft 431 through elongated shaft 420.

Drive assembly 430 further includes a stop ring 438 and first and second biasing members 439a, 439b, each of which is disposed about inner shaft 431. Stop ring 438 is fixedly engaged about inner shaft 431 and disposed within internal bore 413 of proximal hub 410. First biasing member 439a is positioned distally of stop ring 438 and is retained between stop ring 438 and the distal end of proximal hub 410. Second biasing member 439b is positioned proximally of stop ring 438 and is retained between stop ring 438 and the distal end of plunger 435. First biasing member 439a has a first spring constant "KK1" which is less than a second spring constant "KK2" of second biasing member 439b, the importance of which is detailed below.

The use of handle assembly 100 in conjunction with endoscopic assembly 400 is now detailed with reference to FIGS. 8-14 and 22-28. Initially, endoscopic assembly 400 is engaged with handle assembly 100, as detailed above. Since endoscopic assembly 400 is configured for ratcheting use of ratcheting drive assembly 130, ratchet pawl 142 remains disposed in the use position upon engagement of endoscopic assembly 400 with handle assembly 100. More specifically, due to the relative positions and dimensions of ring-shaped aperture 414 of proximal hub 410 and sleeve 152 of bypass assembly 150, as proximal hub 410 is inserted into receiver assembly 170, sleeve 152 is received within ring-shaped aperture 414, thereby enabling sleeve 152 to remain in its distal-most position under the bias of biasing member 154. With sleeve 152 remaining in its distal-most position, ratchet pawl 142 is retained in the use position under the bias of pawl biasing member 146. Thus, as detailed below, ratcheting use of handle assembly 100 and endoscopic assembly 400 is enabled. Once endoscopic assembly 400 and handle assembly 100 are engaged with ratchet pawl 142 remaining in the use position, handle assembly 100 and endoscopic assembly 400 are together ready for use.

In use, trigger 122 is initially disposed in the un-actuated position under the bias of biasing member 127. With trigger 122 disposed in the un-actuated position, drive bar 132 is disposed in a proximal-most position such that ratchet pawl 142 is disposed within distal recess 138 of drive bar 132. Further, with drive bar 132 disposed in the proximal-most position, inner shaft 431 of drive assembly 430 is disposed in a proximal-most position under the bias of first and second biasing members 439a, 439b, respectively. Thus, jaw members 460a, 460b, initially, are disposed in the open position. With jaw members 460a, 460b disposed in the open position, a new, unformed or open surgical clip (not shown) may be located or loaded within jaw members 460a, 460b, or may be otherwise operably positioned (manually or automatically) for insertion therebetween for formation or closure about tissue upon closure of jaw members 460a, 460b. For example, in some embodiments, during firing, a surgical clip is first advanced from elongated shaft 420 between jaw members 460a, 460b and, thereafter, jaw members 460a, 460b are closed to form the surgical clip. In such embodiments, a series of surgical clips may be loaded within elongated shaft 420 for sequential firing in a similar manner. However, other suitable surgical clips and/or configurations for firing thereof are also contemplated.

In order to close, fire, or form the surgical clip loaded between jaw members 460a, 460b, trigger 122 is urged from the un-actuated position to the actuated position. More specifically, grasping portion 123 of trigger 122 is pivoted towards fixed handle portion 112 of housing 110 to urge linkage 128 distally which, in turn, urges drive bar 132 distally. As drive bar 132 is urged distally, ratchet pawl 142 moves out of distal recess 138 of drive bar 132 and into engagement with ratchet rack 136. Once ratchet pawl 142 is engaged with ratchet rack 136, trigger 122 may not return towards the un-actuated position and, thus, drive bar 132 may not return proximally until trigger 122 reaches the actuated position, completing a full actuation stroke thereof.

As drive bar 132 is translated distally, drive bar 132 is advanced through housing 110, receiver assembly 170, and into bore 413 of proximal hub 410 of endoscopic assembly 400. Eventually, drive bar 132 contacts plunger 435 of drive assembly 430 of endoscopic assembly 400. Due to first spring constant "KK1" of first biasing member 439a being less than second spring constant "K2" of second biasing member 439b, as drive bar 132 is initially urged into plunger 435, plunger 435 and inner shaft 431 translate together distally such that first biasing member 439a is compressed while second biasing member 439b remains substantially un-compressed. As inner shaft 431 is translated distally, a surgical clip is first loaded between first and second jaw members 460a, 460b and, thereafter, first and second jaw members 460a, 460b are transitioned from the open position to the closed position to form the surgical clip about tissue, although other configurations are also contemplated.

As noted above with respect to endoscopic assembly 300 (FIGS. 15-21), depending upon the particular endoscopic assembly used, the configuration of the surgical clip being formed, and/or other factors, the required travel distance of inner shaft 431 to fully form the surgical clip may vary. As also mentioned above, once ratchet pawl 142 is engaged with ratchet rack 136, trigger 122 may not return towards the un-actuated position until trigger 122 reaches the actuated position, completing a full actuation stroke thereof. Thus, in order to enable return of trigger 122 to the un-actuated position in instances where the required length of travel of drive bar 132 to fully form the surgical clip is insufficient for ratchet pawl 142 to clear ratchet rack 136 and enter proximal recess 139 of drive bar 132, endoscopic assembly 400 must allow further travel of drive bar 132, as detailed below.

As trigger 122 is further actuated to complete the full actuation stroke thereof, plunger 435 is continued to be driven distally. However, since inner shaft 431 cannot travel further distally, second biasing member 439b is compressed, thus allowing plunger 435 to translate distally independently of inner shaft 431. That is, the compression of second biasing member 439b enables inner shaft 431 to remain in position while the full actuation stroke of trigger 122 is completed.

Upon full actuation of trigger 122, e.g., upon reaching the actuated position of trigger 122, ratchet pawl 142 is moved into proximal recess 139 of drive bar 132. With ratchet pawl 142 disposed within proximal recess 139, trigger 122 may be released and returned to the un-actuated position under the bias of biasing member 127. Thereafter, the above-detailed use may be repeated to close, fire, or form additional surgical clips.

It is contemplated, and within the scope of the present disclosure, that other endoscopic assemblies, including a pair of jaws having a unique and diverse closure stroke length thereof, may be provided for use with handle assembly 100 for ratcheting use or non-ratcheting use, similarly as detailed above with respect to endoscopic assemblies 300, 400 (FIGS. 15-21 and 22-28, respectively). Such a configuration accommodates various different endoscopic assemblies having different configurations and/or different closure stroke lengths while providing a constant actuation stroke length of trigger 122. Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A handle assembly of a reposable surgical clip applier configured to releasably engage at least two different endoscopic assemblies, the handle assembly comprising:
 a housing defining a body portion and a fixed handle portion extending from the body portion;
 a trigger pivotably connected to the housing and movable relative to the fixed handle portion between an un-actuated position and an actuated position;
 a drive bar slidably supported within the body portion of the housing and operably coupled to the trigger such that movement of the trigger from the un-actuated position towards the actuated position translates the drive bar distally through the body portion of the housing, the drive bar including a ratchet rack disposed thereon;
 a ratchet pawl pivotably supported within the housing and movable relative thereto between a use position, wherein the ratchet pawl is positioned to engage the ratchet rack upon distal translation of the drive bar, and a bypass position, wherein the ratchet pawl is displaced from the ratchet rack to inhibit engagement therewith upon distal translation of the drive bar;
 a receiver assembly configured to releasably engage an endoscopic assembly therein; and
 a bypass assembly operably positioned between the receiver assembly and the ratchet pawl and configured such that, upon insertion of a first type of endoscopic assembly into engagement with the receiver assembly, the bypass assembly urges the ratchet pawl to move to the bypass position to disable ratcheting during distal translation of the drive bar, and such that, upon insertion of a second type of endoscopic assembly into engagement with the receiver assembly, the bypass assembly is undisturbed such that the ratchet pawl remains disposed in the use position to enabling ratcheting during distal translation of the drive bar.

2. The handle assembly according to claim 1, wherein the bypass assembly includes a sleeve defining a distal rim configured to interfere with the first type of endoscopic assembly upon insertion of the first type of endoscopic assembly into the receiver assembly such that the first type of endoscopic assembly urges the sleeve proximally to thereby move the ratchet pawl from the use position to the bypass position.

3. The handle assembly according to claim 2, wherein the sleeve of the bypass assembly is configured for insertion into an opening defined within the second type of endoscopic assembly upon insertion of the second type of endoscopic assembly into the receiver assembly such that the sleeve is maintained in position.

4. The handle assembly according to claim 3, wherein the bypass assembly further includes a biasing member configured to bias the sleeve distally such that the sleeve is maintained in position in the absence of proximal urging applied thereto.

5. The handle assembly according to claim 1, further including a pawl biasing member configured to bias the ratchet pawl towards the use position.

6. The handle assembly according to claim 1, wherein the receiver assembly including an inner tubular member configured to releasably receive a proximal portion of the first type of endoscopic assembly and a proximal portion of the second type of endoscopic assembly, the inner tubular member including at least one alignment member configured to align the proximal portion of the endoscopic assembly inserted therein, and at least one engagement member configured to releasably engage the proximal portion of the endoscopic assembly inserted therein.

7. The handle assembly according to claim 1, wherein the drive bar defines a proximal recess disposed proximally of the ratchet rack and a distal recess disposed distally of the ratchet rack.

8. The handle assembly according to claim 7, wherein, in the un-actuated position of the trigger and the use position of the ratchet pawl, the drive bar is positioned such that the ratchet pawl is at least partially disposed within the distal recess.

9. The handle assembly according to claim 8, wherein in an intermediate position of the trigger between the un-actuated and actuated positions thereof, and the use position of the ratchet pawl, the drive bar is positioned such that ratchet pawl is engaged with the ratchet rack to inhibit return of the trigger towards the un-actuated position.

10. The handle assembly according to claim 9, wherein, in the actuated position of the trigger and the use position of the ratchet pawl, the drive bar is positioned such that the ratchet pawl is at least partially disposed within the proximal recess to permit the trigger to be returned to the un-actuated position.

11. A reposable surgical clip applier, comprising:
a handle assembly, including:
a housing defining a body portion and a fixed handle portion extending from the body portion;
a trigger pivotably connected to the housing and movable relative to the fixed handle portion between an un-actuated position and an actuated position;
a drive bar slidably supported within the body portion of the housing and operably coupled to the trigger such that movement of the trigger from the un-actuated position towards the actuated position translates the drive bar distally through the body portion of the housing, the drive bar including a ratchet rack disposed thereon;
a ratchet pawl pivotably supported within the housing and movable relative thereto between a use position, wherein the ratchet pawl is positioned to engage the ratchet rack upon distal translation of the drive bar, and a bypass position, wherein the ratchet pawl is displaced from the ratchet rack to inhibit engagement therewith upon distal translation of the drive bar;
a receiver assembly configured to releasably engage an endoscopic assembly therein; and
a bypass assembly operably positioned between the receiver assembly and the ratchet pawl, the bypass assembly movable between a distal position and a proximal position for moving the ratchet pawl between the use position and the bypass position; and
an endoscopic assembly configured for ratcheting use, the endoscopic assembly including:
a proximal hub insertable into and releasably engagable within the receiver assembly of the handle assembly;
an elongated shaft extending distally from the proximal hub;
an end effector assembly supported at a distal end of the elongated shaft; and
an inner drive assembly disposed within the proximal hub and the elongated shaft and operably coupled to the end effector assembly such that actuation of the inner drive assembly manipulates the end effector assembly,
wherein the proximal hub and the inner drive assembly define an annular gap therebetween, the annular gap configured to receive a portion of the bypass assembly upon insertion of the endoscopic assembly into the receiver assembly such that the bypass assembly is maintained in the distal position upon engagement of the proximal hub within the receiver assembly, thereby maintaining the ratchet pawl in the use position and enabling engagement of the ratchet pawl with the ratchet rack during distal translation of the drive bar.

12. The reposable surgical clip applier according to claim 11, wherein, upon movement of the trigger from the un-actuated position to an intermediate position between the un-actuated position and the actuated position, the drive bar is positioned such that ratchet pawl is engaged with the ratchet rack to inhibit return of the trigger towards the un-actuated position.

13. The handle assembly according to claim 12, wherein the drive bar defines a proximal recess disposed proximally of the ratchet rack and configured such that, upon movement of the trigger to the actuated position, the pawl is disposed at least partially within the proximal recess to permit return of the trigger to the un-actuated position.

14. A reposable surgical clip applier, comprising:
a handle assembly, including:
a housing defining a body portion and a fixed handle portion extending from the body portion;
a trigger pivotably connected to the housing and movable relative to the fixed handle portion between an un-actuated position and an actuated position;
a drive bar slidably supported within the body portion of the housing and operably coupled to the trigger such that movement of the trigger from the un-actuated position towards the actuated position translates the drive bar distally through the body portion of the housing, the drive bar including a ratchet rack disposed thereon;
a ratchet pawl pivotably supported within the housing and movable relative thereto between a use position, wherein the ratchet pawl is positioned to engage the ratchet rack upon distal translation of the drive bar, and a bypass position, wherein the ratchet pawl is displaced from the ratchet rack to inhibit engagement therewith upon distal translation of the drive bar;
a receiver assembly configured to releasably engage an endoscopic assembly therein; and
a bypass assembly operably positioned between the receiver assembly and the ratchet pawl, the bypass assembly movable between a distal position and a proximal position for moving the ratchet pawl between the use position and the bypass position; and
an endoscopic assembly configured for non-ratcheting use, the endoscopic assembly including:
a proximal hub insertable into and releasably engagable within the receiver assembly of the handle assembly, the proximal hub defining a proximally-facing surface;
an elongated shaft extending distally from the proximal hub;
an end effector assembly supported at a distal end of the elongated shaft; and
an inner drive assembly disposed within the proximal hub and the elongated shaft and operably coupled to the end effector assembly such that actuation of the inner drive assembly manipulates the end effector assembly, wherein the proximally-facing surface of the proximal hub is positioned such that, upon insertion of the endoscopic assembly into the receiver assembly, the proximally-facing surface is urged into contact with the bypass assembly to move the bypass assembly from the distal position to the proximal position to thereby pivot the ratchet pawl from the use position to the bypass position to inhibit engagement of the ratchet pawl with the ratchet rack during distal translation of the drive bar.

15. The reposable surgical clip applier according to claim 14, wherein the trigger is permitted to return towards the actuated position at each point between the un-actuated position and the actuated position.

16. A reposable surgical clip applying system, comprising:
a handle assembly, including:
a housing defining a body portion and a fixed handle portion extending from the body portion;
a trigger pivotably connected to the housing and movable relative to the fixed handle portion between an un-actuated position and an actuated position;
a drive bar slidably supported within the body portion of the housing and operably coupled to the trigger such that movement of the trigger from the un-actuated position towards the actuated position translates the drive bar distally through the body portion of the housing, the drive bar including a ratchet rack disposed thereon;
a ratchet pawl pivotably supported within the housing and movable relative thereto between a use position, wherein the ratchet pawl is positioned to engage the ratchet rack upon distal translation of the drive bar, and a bypass position, wherein the ratchet pawl is displaced from the ratchet rack to inhibit engagement therewith upon distal translation of the drive bar;
a receiver assembly configured to releasably engage an endoscopic assembly therein; and
a bypass assembly operably positioned between the receiver assembly and the ratchet pawl, the bypass assembly movable between a distal position and a proximal position for moving the ratchet pawl between the use position and the bypass position;
a first endoscopic assembly configured for ratcheting use, the first endoscopic assembly including:
a proximal hub insertable into and releasably engagable within the receiver assembly of the handle assembly;
an elongated shaft extending distally from the proximal hub;
an end effector assembly supported at a distal end of the elongated shaft; and
an inner drive assembly disposed within the proximal hub and the elongated shaft and operably coupled to the end effector assembly such that actuation of the inner drive assembly manipulates the end effector assembly,
wherein the proximal hub and the inner drive assembly define an annular gap therebetween, the annular gap configured to receive a portion of the bypass assembly upon insertion of the first endoscopic assembly into the receiver assembly such that the bypass assembly is maintained in the distal position upon engagement of the proximal hub within the receiver assembly, thereby maintaining the ratchet pawl in the use position and enabling engagement of the ratchet pawl with the ratchet rack during distal translation of the drive bar; and
a second endoscopic assembly configured for non-ratcheting use, the second endoscopic assembly including:
a proximal hub insertable into and releasably engagable within the receiver assembly of the handle assembly, the proximal hub defining a proximally-facing surface;
an elongated shaft extending distally from the proximal hub;
an end effector assembly supported at a distal end of the elongated shaft; and
an inner drive assembly disposed within the proximal hub and the elongated shaft and operably coupled to the end effector assembly such that actuation of the inner drive assembly manipulates the end effector assembly,
wherein the proximally-facing surface of the proximal hub is positioned such that, upon insertion of the second endoscopic assembly into the receiver assembly, the proximally-facing surface is urged into contact with the bypass assembly to move the bypass assembly from the distal position to the proximal position to thereby pivot the ratchet pawl from the use position to the bypass position to inhibit engagement of the ratchet pawl with the ratchet rack during distal translation of the drive bar.

17. The reposable surgical clip applying system according to claim 16, wherein, upon movement of the trigger from the un-actuated position to an intermediate position between the un-actuated position and the actuated position with the first endoscopic assembly engaged with the handle assembly, the drive bar is positioned such that ratchet pawl is engaged with the ratchet rack to inhibit return of the trigger towards the un-actuated position, and wherein, with the second endoscopic assembly engaged with the handle assembly, the trigger is permitted to return towards the actuated position at each point between the un-actuated position and the actuated position.

* * * * *